(12) United States Patent
Roizman et al.

(10) Patent No.: US 6,410,704 B1
(45) Date of Patent: *Jun. 25, 2002

(54) METHODS AND COMPOSITIONS FOR THE PREPARATION AND USE OF A HERPES PROTEASE

(75) Inventors: Bernard Roizman; Fenyong Liu, both of Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/176,320

(22) Filed: Jan. 3, 1994

Related U.S. Application Data

(63) Continuation of application No. 07/705,814, filed on May 24, 1991, now abandoned.

(51) Int. Cl.[7] .............................................. C07H 21/04
(52) U.S. Cl. .................... 536/23.2; 536/23.1; 536/23.2; 536/24.1; 435/69.1; 435/6; 435/212; 435/235.1; 435/320.1; 435/226; 435/230.1; 435/219; 435/815; 424/230.1
(58) Field of Search ................................ 435/69.1, 212, 435/219, 240.2, 320.1, 235.1, 6, 226, 815; 536/23.2, 24.1, 24.2, 23.1; 424/230.1

(56) References Cited

PUBLICATIONS

Sambrook, J. et al. *Molecular Cloning: A Laboratory Manual*, 2nd Edition. pp. 14.2–14.5 (1989).*
Alberts, B. et al., *Molecular Biology of the Cell* (1983) Garland Publishing, Inc., pp. 98–103.*
Lewin, B. *Genes*, Third Ed. (1987) John Wiley & Sons, Inc., pp. 41–48, 57–60.*
Stryer, L. *Biochemistry*, Third Ed. (1988) W.H. Freeman and Company, pp. 71–82*
Sambrook, J. et al. *Molecular Cloning: A Laboratory Manual* (1989) pp. 16.2–16.31 and F.1–F.11.*
Liu & Riozman, J. Virol., 65(1):206–212, 1991.
Newcomb & Brown, J. Virol., 65(2):613–620, 1991.
Schenk et al., J. Virol.,65(3):1525–1529, 1991.
Gibson et al., J. Virol., 64(3):1241–1249, 1990.
Chou & Roizman, J. Virol., 64(3):1014–1020, 1990.
Bjorck et al., Nature, 337:385–386, 1989.
Bjorck et al., J. Virol., 64(2):941–943, 1990.
McGeoch et al., J. Gen. Virol., 69:1531–1574, 1988.
Corey & Spear, N. Engl. J. Med., 314(11):686–691, 1986.
Holland et al., J. Virol., 49(3):947–959, 1984.
Braun et al., J. Virol., 49(1):142–153, 1984.
Braun et al., J. Virol., 46(1):103–112, 1983.
Preston et al., J. Virol., 45(3):1056–1064, 1983.
Post et al., Cell, 24:555–565, 1981.
Gibson & Roizman, J. Virol., 13(1):155–165, 1974.
Gibson & Roizman, J. Virol., 10(5):1044–1052, 1972.

* cited by examiner

Primary Examiner—Christopher S. F. Low
Assistant Examiner—Hope A. Robinson
(74) Attorney, Agent, or Firm—Fulbright & Jaworski LLP

(57) ABSTRACT

The present invention relates to the identification and purification of a herpes protease and a nucleic acid segment coding for two proteins. The first protein is the herpes protease which is able to cleave itself and also cleave the second protein. This protease is required for the assembly of the herpes virus capsid, therefore is essential for replication. The second protein has previously been designated as the family of proteins in viral infected cells, ICP35. The protease and its substrates are encoded by overlapping nucleic acid segments. This invention also relates to a promoter sequence for the second protein. Methods are presented of producing a viral protease, screening a protease inhibitor which may be used in a drug designed for the treatment of herpes disease, methods for treating herpes and other viral infections wherein the virus employs a protease substantially similar to the herpes protease, for capsid production. Methods for detecting herpes infections and other viral infections are also disclosed.

14 Claims, 20 Drawing Sheets

```
        MetAlaAlaAspAlaProGlyAspArgMetGluGluProLeuProAspArgAlaValPro
  1     ATGGCAGCCGATGCCCCGGGAGACCGGATGGAGGAGCCCCTGCCCGACAGGCCTGCCC
        TACCGTCGGCTACGGGGCCCTCTGGCCAGCCTCCTCGGGACGGGCTGTCCCGGCACGGG

IleTyrValAlaGlyPheLeuAlaLeuTyrAspSerGlyAspSerGlyGluLeuAlaLeu
 61     ATTTACGTGGCTGGTGGTTTTTGCCCTGTATGACAGCGGGGACTCGGGGAGTTGGCATTG
        TAAATGCACCGACCACCAAAAACGGGACATACTGTCGCCCCTGAGCCCCTCAACCGTAAC

AspProAspThrValArgAlaAlaAlaLeuProProAspAsnProLeuProIleAsnValAsp
121     GATCCGGATACGGTGCGGGCGGCCGCTCCGCCTGATAACCCACTCCCGATTAACGTGGAC
        CTAGGCCTATGCCACGCCCGCCGGCGAGGCGGACTATTGGGTGAGGGCTAATTGCACCTG

HisArgAlaGlyCysGluValGlyArgValLeuAlaValValAlaAspProArgGlyPro
181     CACCGCGCTGGCTGCGAGGTGGGGCGGGTGCTGGCCGTTGTTGCGGACCCCCGGGGGCCG
        GTGGCGCGACCGACGCTCCACCCGCCACGACCGGCAACGACCAGCTGCTGGGGGCCCGGC

PhePheValGlyLeuIleAlaCysValGlnLeuGluArgValLeuGluThrAlaAlaSer
241     TTTTTTGTGGGGCTGATCGCCTGTGTGCAGCTGGAGCGCGTCCTGGAGACGGCCGCCAGC
        AAAAAACACCCCGACTAGCGGACACGTCGACCTCGCCAGGACCTCTGCCGGCGGTCG

AlaAlaIlePheGluArgArgGlyProProLeuSerArgGluArgLeuLeuLeuTyrLeu
301     GCTGCGATTTTCGAGCGCCGCGGCCCGCCGCTCTCCCGGGAGGAGCGCCTGTTGTACCTG
        CGACGCTAAAAGCTCGCGGCGCCGGGCGGCGAGAGGGCCCTCCTCGCGGACAACATGGAC
```

FIG.1B(I)

```
      IleThrAsnTyrLeuProSerValSerLeuAlaThrLysArgLeuGlyGlyGluAlaHis
361   ATCACCAACTACTACCTGCCCTCGGTCTCCCTGGCCACAAAACGCCTGGGGGGGAGGCCAC
      TAGTGGTTGATGATGGACGGGAGCCAGAGGGACCGGTGTTTTGCGGACCCCCCCTCCGGTG

ProAspArgThrLeuPheAlaHisValAlaLeuCysAlaIleGlyArgArgLeuGlyThr
421   CCCGATCGCACGCTGTTCGCGCACGTCGCGCTCTGTGCCATCGGGCGCCGGCTCGGCACT
      GGGCTAGCGTGCGACAAGCGCGTGCAGCGCGAGACACGGTAGCCCGCGGCCGAGCCGTGA

IleValThrTyrAspThrGlyLeuAspAlaAlaIleAlaAlaProPheArgHisLeuSerPro
481   ATCGTCACCTACGACACCGGTCTCGACGCCGCCATCGCGGCCCCTTTCGCCACCTGTCGCCG
      TAGCAGTGGATGCTGTGGCCAGAGCTGCGGCGGTAGCGCCGGGGAAAGCGGTGGACAGCGGC

AlaSerArgGluGlyAlaArgArgLeuAlaAlaGluLeuAlaLeuSerGlyArg
541   GCGTCTCGCGAGGGCGCCCGGAGGCTGGCCGCCGAGCTCGCGCTGTCCGGGCGC
      CGCAGAGCGCTCCCCGCGGGCCTCCGACCGGCGCTCGAGCGCGACAGGCCCGCG

ThrTrpAlaProGlyValGluAlaLeuThrHisThrLeuLeuSerThrAlaValAlaAsnAsn
601   ACCTGGGCGCCCGGCGTGGAGGCGCTGACCCACACGCTGCTTTCCACCGCCGTTAACAAC
      TGGACCCGCGGGCCGCACCTCCGCGACTGGGTGTGCGACGAAAGGTGGCGGCAATTGTTG

MetMetLeuArgAspArgTrpSerLeuValAlaGluArgArgGlnAlaGlyIleAla
661   ATGATGCTGCGGGACCGCTGGAGCCTGGTGGCCGAGCGGCGCCAGGCCGGGATCGCC
      TACTACGACGCCCTGGCGACCTCGGACCACCGGCTCGCCGCGGTCCGGCCCTAGCGG
```

FIG.1B(II)

```
         GlyHisThrTyrLeuGlnAlaSerGluLysPheLysMetTrpGlyAlaGluProValSer
  721    GGACACACCTACCTCCAGGCGAGCGAAAAATTCAAAATGTGGGGCGGAGCCTGTTTCC
         CCTGTGTGGATGGAGGTCCGCTCCGCTTTTTAAGTTTTACACCCCGCCTCGGACAAAGG

AlaProAlaArgGlyTyrLysAsnGlyAlaProGluSerThrAspIleProProGlySer
  781    GCGCCGGCCCGGGGTATAAGAACGGGGCCCCGGAGTCCACGGACATACCCGGCCTCG
         CGCGGCCGGGCCCCATATTCTTGCCCCGGGGCCTCAGGTGCCTGTATGGGGCCGAGC

IleAlaAlaAlaProGlnGlyAspArgCysProIleValArgGlnArgGlyValAlaLeu
  841    ATCGCTGCCGCGCCAGGGTGACCGGTGCCCAATCGTCCGTCAGCCGCGGGTCGCCTTG
         TAGCGACGGCGCGGGGTCCCACTGGCCACGGGTTAGCAGGCAGTCGGCGCCCAGCGGAAC

SerProValLeuProProMetAsnProValProThrSerGlyThrProAlaProAlaPro
  901    TCCCCGGTACTGCCCCCCATGAACCCCGTTCCGACATCGGGCACCCCGGCCCCCGCCG
         AGGGGCCATGACGGGGGGTACTTGGGCAAGGCTGTAGCCCGTGGGGCCGGGGGCGGCC

ProGlyAspGlySerTyrLeuTrpIleProAlaSerHisTyrAsnGlnLeuValAlaGly
  961    CCCGGCGACGGGAGCTACCTGTGGATCCCGGCCTCCCATTACAACCAGCTCGTCGCCGGC
         GGGCCGCTGCCCTCGATGGACACCTAGGGCCGGAGGGTAATGTTGGTCGAGCAGCGGCCG

HisAlaAlaProGlnProHisSerAlaPheGlyPheProAlaAlaAlaGlySer
 1021    CATGCCGCCCCCAACCCCAGCGCATTCCGGTTTGGTTTCCCGGCTGCGGGGTCC
         GTACGGCGGGGGTTGGGGTCGGCGTAAGGCCAAACCAAAGGGCCGACGCCCCAGG

FIG.1B(III)
```

```
      ValAlaTyrGlyProHisGlyAlaGlyLeuSerGlnHisTyrProProHisValAlaAlaHis
1081  GTGGCCTATGGCCCTCACGGTGCGGTGTCTTTCCCAGCATTACCCTCCCCACGTCGCCCAT
      CACCCGGATACCCGGAGTGCCACGCCACAGAAAGGGTCGTAATGGGAGGGTGCAGGGGTA

GlnTyrProGlyValLeuPheSerGlyProSerGlyProLeuGluAlaGlnIleAlaAlaLeu
1141  CAGTATCCCGGGGTGCTGTTCTCGGACCCAGCCAGCTGAGGGGCAGATAGCCGCGTTG
      GTCATAGGGCCCCACGACAAGAGCCCTGGGTCGGTGAGCTCCGGTCTATCGGGCAAC

ValGlyAlaIleAlaAlaAspArgGlnAlaGlyGlyGlnProAlaAlaGlyAspProGly
1201  GTGGGGGCCATAGCCGCGGACCGCCAGGCGGTCAGCCGCGGGGAGACCCTGGG
      CACCCCCGGTATCGGCGCCTGGCGGTCCGCCAGTCGGGCGCCCCTCTGGACCC

ValArgGlySerGlyLysArgArgTyrGluAlaGlyProSerGluSerTyrCysAsp
1261  GTCCGGGGGTCGGGAAAGCGTCGCCGGTACGAGGGGCCGTCGGAGTCCTACTGCGAC
      CAGGCCCCCAGCCCTTTCGCAGCGGCCATGCTCCGCCAGCCTCAGGATGACGCTG

GlnAspGluProAspAlaAspTyrProTyrTyrProGlyGluAlaArgGlyAlaProArg
1321  CAGGACGAACCGGACGCCGACTACCCCTACTACCCCGGGGAGGCTCGCAGGCGCCGC
      GTCCTGCTTGCCTGCCGCTGATGGGGATGATGGGGCCCCTCCGAGCTCCGGCGGCG

GlyValAspSerArgArgAlaAlaArgHisSerProGlyThrAsnGluThrIleThrAla
1381  GGGGTCGACTCCCGGCGCGCCGCCATTCTCCCGGACCAACGAGACCATCACGGCG
      CCCCAGCTGAGGGCCGCGCGGCGGTAAGAGAGGCCCTGGTTGCTCTGGTAGTGCCGC

FIG.1B (IV)
```

```
       LeuMetGlyAlaValThrSerLeuGlnGlnGluLeuAlaHisMetArgAlaArgThrSer
1441   CTGATGGGGGCGGTGACGTCTCTGCAGCAGGAACTGGCGCACATGCGGGCTCGGACCAGC
       GACTACCCCCGCCACTGCAGAGACGTCGTCCTTGACCGCGTGTACGCCCGAGCCTGGTCG

AlaProTyrGlyMetTyrThrProValAlaHisTyrArgProGlnValGlyGluProGlu
1501   GCCCCTATGGAATGTACACGCCGGTGGCACATTACCGCCCTCAGGTGGGAGCCCGAA
       CGGGGATACCTTACATGTGCGGCCACCGTGTAATAGCGGGAGTCCACCCCTCGGCCTT

ProThrThrThrHisProAlaLeuCysProProGluAlaValTyrArgProProProHis
1561   CCAACAACGACCACCCGGCCCTTTGTCCCCGGAGGCCGTGTATCGCCCCACCACAC
       GGTTGTTGCTGGTGGGCGGGAAACAGGGGCCTCCGGCACATAGCGGGGTGGTGTG

SerAlaProTyrGlyProProGlnGlyProAlaSerHisAlaProThrProProTyrAla
1621   AGCGCCCCCTACGGTCCTCCCCAGGGTCCGGCGTCCCATGCCCCCACTCCCCCCTATGCC
       TCGCGGGGGATGCCAGGAGGGGTCCCAGGCCGCAGGGTACGGGGTGAGGGGGATACGG

ProAlaAlaCysProProGlyProProProProCysProSerThrGlnThrArgAla
1681   CCAGCTGCCTGCCCCGGCCCCCGGCCCCCATGTCCTTCCACCAGACGCGGCC
       GGTCGACGGACGGGGCCGGGGCCGGGGGTACAGGAAGGTGGTCTGCGCCGG

ProLeuProThrGluProAlaPheProProAlaAlaThrGlySerGlnProGluAlaSer
1741   CCTCTACCGACGGAGCCCGCCTTCCCCCCGCCACCGGATCCCAACCGGAGGCATCC
       GGAGATGGCTGCCTCGGGCGGCAAGGGGGGCGGTGGCCTAGGGTTGGCCTCCGTAGG
```

FIG.1B(V)

```
        AsnAlaGluAlaGlyAlaLeuValAlaAsnAlaSerSerAlaAlaHisValAspValAspThr
1801    AACGCGGAGGCCGGGGCCCTTGTCAACGCCAGCAGCGCCGCACACGTGGACGTTGACACG
        TTGCGCCTCCGGCCCCGGGAACAGTTGCGGTCGTCGCGGTGTGTGCACCTGCAACTGTGC

AlaArgAlaAlaAspLeuPheValSerGlnMetMetGlyAlaArg
1861    GCCCGCGCCGCCGATTTGTTCGTCTCTCAGATGATGGGGCCCGC
        CGGGCGCGGCGGCTAAACAAGCAGAGAGTCTACTACCCCCGGGCG
```

FIG. IB (VI)

METHODS AND COMPOSITIONS FOR THE PREPARATION AND USE OF A HERPES PROTEASE

This application is a continuation of application Ser. No. 07/705,814, filed May 24, 1991 now abandoned.

The government may own certain rights in the present invention pursuant to grants from the National Cancer Institute (CA47451) and the National Institute for Allergy and Infectious Diseases (AI124009 and AI1588-11), the United States Public Health Service.

BACKGROUND OF THE INVENTION

1. Field of the Invention

The present invention relates to the identification and purification of herpes proteases and to nucleic acid segments coding for such proteases. The present invention also relates to methods of selecting candidate substances that are able to inhibit the function of these proteases and the use of such inhibitors to detect and treat viral infections.

2. Description of Related Art a. Viral Infections Pose Major Health Problems Treatment and prevention of viral infections is a major medical goal. To understand the state of the art in developing methods of treating and preventing viral infections, it is important to understand the structure and function of infectious virus. A virus is a small genetic element that contains either single or double-stranded DNA or RNA and can alternate between two distinct states: intracellular and extracellular. A virus is a obligatory intra-cellular parasite that cannot reproduce by itself. In effect, the virus takes over the biosynthetic machinery of the host cell and uses it for viral synthesis. Some of the protein products of the viral DNA are special enzymes or inhibitory factors that stop host cell metabolism, but most viral-encoded proteins are used in the construction of new virions. Protein synthesis is directed by the virus to produce necessary components for its replication and packaging, e.g. the capsid. These components must be assembled in an order depending on the virus, and new particles must escape from the cell if they are to infect other cells.

The general steps of the intracellular viral replication (lytic cycle) are:

1. attachment of the virus to a host cell (absorption);
2. penetration of the virus or its nucleic acid into the host cell;
3. replication of the viral nucleic acid;
4. production of viral proteins and other essential components;
5. assembly of viral nucleic acid and protein components; and
6. release of mature virion particles from the host cell.

The overall result of the lytic cycle is new virus particles and dead host cells because the virus has appropriated the vital forces of the host. In certain types of infection, such as that caused by herpes, there may be a latent period wherein the virus resides in the host cell.

Elucidation of viral genetic systems opens the door to investigations on the mechanisms of viral infection and replication which are not simply of academic interest, but are directed toward detection, prevention, and treatment of viral caused diseases. Host resistance to viral infection may occur through absence of a viral-receptor site to prevent attachment of the virus to the host cell; destruction of the viral nucleic acids after they are injected into the host cell, for example, by cleavage of viral nucleic acids by host enzymes; inhibition of essential viral protein synthesis; or destruction of viral proteins after their formation in the host cell.

Development of antiviral drugs to supplement natural resistance is a major commercial objective whose goal is to counteract the devastating effects of many viral infections on humans. Unfortunately, treatments available to date are inadequate for most types of virus. For example, interferons are cellular antiviral substances, low molecular weight proteins, that prevent viral multiplication. However, interferons tend to be host specific, not viral specific, and have no effect on host cells already infected. Also, they can be toxic at high concentrations.

The target of antiviral drugs may be enzymes uniquely specified by the virus. For example, a major target for attack on HIV infections which cause AIDS, is the enzyme reverse transcriptase. Inhibiting this enzyme effects blockage of viral replication. Unfortunately, resistance develops to these drugs, e.g. to AZT, and is a major limitation of such treatment. The anti-herpes simplex virus drugs currently on the market are directed against enzymes which synthesize viral DNA (e.g. acyclovir). Because of emergence of resistance to these drugs, there is considerable interest in new targets.

Production of viral proteins is of particular interest as a stage where the virus may be attacked. In the extracellular or infectious state, the basic structure of viruses consists of a nucleic acid core surrounded by proteins (nucleocapsid). Some viruses also have an envelope that is external to the nucleocapsid, and contains lipids and protein. The protein coat is called the capsid. Many different proteins may constitute the capsid, depending on the virus. Some viruses encode 3–10 proteins, others more than 200. Virus particles are called virions; their role is to protect the viral nucleic acid when transferred from the cell in which it replicated to a new host cell. After transfer to the host cells, the viral intracellular state begins, and replication of the virus is potentiated. A number of non-herpes viruses appear to express proteases with cleavage site specificity which are potential targets for therapeutic intervention. However, no such protease has previously been identified for the herpes virus, a particularly widespread infectious agent for which treatment and prevention methods are grossly inadequate.

b. The Herpes Family

The family of herpes virus includes animal viruses of great clinical interest because they are the causative agents of many diseases. Epstein-Barr virus has been implicated in cancer initiation; cytomegalovirus is the greatest infectious threat to AIDS patients; and Varicella Zoster Virus, is of great concern in certain parts of the world where chicken pox and shingles are serious health problems. A worldwide increase in the incidence of sexually transmitted herpes simplex (HSV) infection has occurred in the past decade, accompanied by an increase in neonatal herpes. Contact with active ulcerative lesions or asymptomatically excreting patients can result in transmission of the infective agent. Transmission is by exposure to virus at mucosal surfaces and abraded skin, which permit the entry of virus and the initiation of viral replication in cells of the epidermis and dermis. In addition to clinically apparent lesions, latent infections may persist, in particular in nerve cells. Various stimuli may cause reactivation of the HSV infection. Consequently, this is a difficult infection to eradicate. This scourge has largely gone unchecked due to the inadequacies of treatment modalities.

c. Herpes Simplex Virus (HSV)

Herpes simplex viruses subtypes 1 and 2 (HSV-1, HSV-2), are herpes viruses that are among the most common infectious agents encountered by humans (Corey and Spear, 1986; Whitley, 1990). These viruses cause a broad spectrum of diseases which range from relatively insignificant and nuisance infections such as recurrent herpes simplex labialis, to severe and life-threatening diseases such as herpes simplex encephalitis (HSE) of older children and adults, or the disseminated infections of neonates. Clinical outcome of herpes infections is dependent upon early diagnosis and prompt initiation of antiviral therapy. However, despite some successful therapy, dermal and epidermal lesions recur, and HSV infections of neonates and infections of the brain are associated with high morbidity and mortality. Earlier diagnosis than is currently possible would improve therapeutic success. In addition, improved treatments are desperately needed.

Extrinsic assistance has been provided to infected cells, in particular, in the form of chemicals. For example, chemical inhibition of herpes viral replication has been effected by a variety of nucleoside analogues such as 5-fluorodeoxyuridine (FUDR), 5-iododeoxyuridine, 5-iododeoxyuridine, thymine arabinoside, and the like. Some protection has been provided in experimental animal models by polyspecific or monospecific anti-HSV antibodies, HSV-primed lymphocytes, and cloned T cells to specific viral antigens (Corey and Spear, 1986). However, no satisfactory treatment has been found.

Proteases have not been identified in the herpes viruses, but there is some knowledge of the biology of the herpes virus family. Herpes viruses are double stranded DNA viruses that replicate in host cell nuclei. The herpes virion is constituted from over 30 different proteins which are assembled within the host cell. About 6–8 are used in the capsid. The preferred host cells for herpes viruses are vertebrate cells.

The herpes simplex virus 1 (HSV-1) the genome specifies an abundant capsid protein complex which in denaturing gels forms multiple bands due to different molecular weights of the component proteins. Some preliminary identification of these proteins has been reported. A set of herpes simplex virus 1 (HSV-1) capsid proteins was reported by Gibson and Roizman (1972, 1974). A genetically and immunologically related family of viral capsid proteins identified by their migration bands in denaturing gels has been designated infected-cell proteins 35(ICP35). (Braun et al., 1983, 1984) At least four major and a number of minor bands in one-dimensional denaturing polyacrylamide gels, and numerous spots in two-dimensional gels, have been reported.

Braun et al. (1984) using a panel of monoclonal antibodies exemplified by H745 reported that ICP35 proteins are processed post-translationally into at least 6 species (ICP35a,b,c,d,e,f) differing in electrophoretic mobility on SDS polyacrylamide gels. Although characterized by different molecular weights, this group of virus polypeptides are detected by the same monoclonal antibodies and are coded by a region in the HSV-1 genome. Empty capsids do not contain these polypeptides. A set of proteins possibly analogous to ICP35 was reported by Preston et al. (1983).

Nucleotide sequencing has been performed on the HSV-1 genome, and attempts, generally unsuccessful, have been made to correlate various capsid proteins to sequences of the genome. It has been proposed that the ICP35 proteins are encoded by the open reading frame designated $U_L26$ (McGeoch, et al., 1988). In the present invention it is shown that this prediction was incomplete and not correct. Crude mapping of the region encoding ICP35 was attempted by Braun et al. (1984) on the basis of the analysis of HSV-1× HSV-2 intertypic recombinants. These authors proposed that ICP35 is encoded by a region located between the genes specifying thymidine kinase ($U_L23$) and glycoprotein B ($U_L27$). This is not a very specific prediction because it covers an area including four genes.

The present invention resulted from a successful search for a new virus target for therapy. The search began by choice of the HSV-1 ICP35 protein family as a substrate. A protease target for antiviral chemotherapy, in particular, as applied to herpes virus infections, was identified in this fashion. Methods of preparing and detecting the protease, methods for selecting inhibitors of the protease, as well as detection and treatment protocols based on inhibiting the protease, are also aspects of the present invention.

SUMMARY

This invention relates to the identification, purification and manipulation of viral proteases to effect treatment and prevention of viral infections. The proteases of the present invention are further defined as serine proteases with the properties expected of this category of protease. A serine protease is an enzyme which catalyzes the hydrolysis of peptide bonds in which there is an essential serine residue at the active site. (White, Handler and Smith, 1973). Differences among serine proteases include an arrangement of a triad of catalytic residues, e.g., in both trypsin and subtilisin serine proteases, Asp, His, and Ser are the amino acids of the catalytic triad. However, in trypsin-like serine proteases, they are arranged His, Asp, Ser, whereas subtilisin-like proteases are arranged Asp, His, Ser. There are also differences in the relative spacing of these key residues. In addition, there are other evolutionarily conserved features of these proteases which allow them to be identified as serine proteases and subsequently classified. The presence of the catalytically important Asp, His, and Ser residues are the crucial tests, however, for membership and classification in the serine proteases.

The proteases of the present invention appear to be essential for development of the capsid of the virus. Consequently, inhibiting the protease action will lead to disruption of the lytic cycle of the virus. Obviously, such proteases are optimal targets for antiviral therapy. In particular, the target is useful for attacks on the herpes virus for which no protease has heretofore been reported. The present invention relates more particularly to the identification, purification, and manipulation of herpes serine proteases, and to the use of inhibitors of the proteases to detect and treat herpes infections.

In an illustrative embodiment, a protease has been purified from HSV-1, a subtype of the herpes simplex virus. The apparent molecular weight of this protease as determined by SDS-polyacrylamide PAGE gel electrophoresis is approximately 75–85 kd, generally about 80 kd. The herpes protease is further characterized as having an amino acid sequence of approximately 450–635 amino acids. However, these ranges are flexible. For example, the 635 amino acid sequence SEQ ID NO: 2 may have at least 125 amino acids removed from its carboxyl end and still maintain its serine protease activity. In the 635 amino acid embodiment SEQ ID NO: 2 the protease cleavage site is located at a position about 18–25 amino acids from the carboxyl terminus, preferably about 20 amino acid from the carboxyl terminus. The proteases are obtained either from cells injected with HSV-1 and 2, cells transfected with a DNA sequence encoding the protease, or in purified form by being synthesized in vitro in cell free systems, using a reticulocyte lysate, for example, from a rabbit. The latter is a "ribosome machine" that permits production of a purified protein encoded by the nucleic acid sequence added to the "machine." After synthesis of the protein, the protein will migrate as a single band on a denaturing gel and is readily detected with $^{35}$S labelled methionine. After about 5 hours of protein synthesis, two bands will result. As demonstrated in subsequent sections, the second band is a self-cleavage product of the first.

The present invention also relates to nucleic acid segments which are capable of coding for the herpes proteases described herein. In an illustrative embodiment, extensive manipulation of nucleic acid sequences within the HSV-1 genome has revealed the secrets of viral mechanisms and allowed isolation and purification of useful nucleic acid segments and their expression products. Examples of such manipulation include incorporation of selected segments of the nucleic acid sequence with appropriate promoters and tracers into plasmids to determine the actions and interactions of the genetic regions, their expression products, and mechanisms of control over their expression. These specially designed plasmids are aspects of the invention.

Another aspect of this invention is the coding domain in the nucleic acid segment for the family of herpes simplex virus 1 capsid proteins designated ICP35. This newly defined coding region has been designated $U_L26.5$. In an illustrative embodiment of the coding sequence for ICP35 proteins, the segment has been demarcated by the restriction endonuclease cleavage sites Hpa-I and Pst-I. These two cleavage sites are located at map positions +832 and +2761. These map locations are defined as distances from the transcription initiation site of the $U_L26$ open reading frame in the HSV-1 genome. This position has been designated +1. The gene coding for the ICP35 proteins also comprises those sequences that are downstream from the KpnI site which is at map position +2104, and continue all the way to a poly A site at position +2138.

The nucleic acid segments in the present invention are further defined as having overlapping open reading frames for the protease and the ICP35 proteins. These overlapping segments are "3'co-terminal." The first segment SEQ ID NO: 1, the longer of the two, codes for a first protein. This first protein has a molecular weight of approximately 75–85 kd. The second open reading frame, the smaller of the two overlapping open reading frame sequences encodes a second protein that has an apparent approximate molecular weight of 40–55 kd as determined by SDS polyacrylamide gel electrophoresis, preferably 45 kd. The first protein is defined to encode a least a proteolytic module which is capable of cleaving an amino acid sequence in accordance with serine protease action. The substrate capable of being cleaved may be either the protease sequence itself that is encoded by the $U_L26$ gene, or the ICP35 precursor proteins, which have previously been designated ICD35 c, d based on migration in one and two dimensional gels.

A nucleic acid segment, either DNA or RNA, coding for the second protein includes approximately 990 base pairs in an HSV-1 embodiment. In certain applications, the segment encodes need include only the sequences which upon cleavage will yield ICP35 e and f. In other applications, only the cleavage site per se may be desired to be encoded, for example in the candidate inhibitor assay described subsequently. In an exemplary embodiment, the nucleic acid segment includes those segments essentially as set forth in FIG. 1A, line 5, of the present specification, or its functional equivalent. A functional equivalent for purposes of this invention may be defined as a segment of nucleic acids which encodes an amino acid sequence that contains a catalytic serine protease coding domain capable of producing a protease which cleaves ICP35. The nucleic acid segment may include a sequence either smaller or larger than those illustrated in FIG. 1, for example, it may correspond to an approximately 14 nucleotide base pair long region which is capable of hybridizing to the nucleic acid segments of FIG. 1 under stringent conditions. Small segments such as this may be used as probes to detect the presence of the protease coding region.

A nucleic acid segment may also be an mRNA sequence for the protease or the ICP35 proteins. The mRNA for the latter is transcribed at approximate nucleotide position +1000 (a designated distance from the herpes $U_L26$ transcription initiation site which is designated +1) to position +2138. An mRNA is translated from the methionine initiation codon which is located at +1099. Smaller or larger segments are also contemplated depending on the use to which the segment is employed. These mRNA segments are useful to synthesize the ICP35 cleavage site.

Various nucleic acid segments within the herpes genome have been isolated and cloned. A nucleic acid segment coding for a herpes protease may be obtained from the herpes genome from a region corresponding to map locations of the $U_L26$ herpes open reading frame SEQ ID NO: 1. A smaller segment contained within the protease coding segment lies between the thymidine kinase gene and glycoprotein gB gene and includes a DNA sequence from position +832 to +2138. This coding sequence not only may be expressed as the ICP35 herpes capsid family proteins, but includes a promoter sequence for regulating the ICP35 coding sequence.

The ICP35 promoter has been isolated and shown to be an extremely active promoter, as is evidenced by the observation that increased numbers of copies of the substrate are produced by the ICP35 encoding unit compared to the production of the protease from the longer $U_L26$ open reading frame. It includes between 135 and 168 base pairs and maps between position +832 and +1000 in the first open reading frame of $U_L26$. This promoter region is capable of initiating expression of the ICP35 proteins. It is also useful in driving expression at an increased rate of other nucleic acid sequences, for example herpes simplex genes $U_S5$ and $U_L10$.

Isolation and manipulation of the coding sequence for the ICP35 proteins was an important achievement of the present invention because these proteins are used in construction of the herpes virus capsid. To become functional members of the capsid, the ICP35 protein precursor ICP35 c, d must be cleaved by the herpes protease produced by the $U_L26$ coding sequence, to yield e and f. This protease is capable of effecting cleavage of the precursor proteins even when both genes encoding for the protease and the precursor are in a trans position.

The nucleic acid segments of the present invention may be carried in a recombinant expression vector capable of expressing virus serine proteases which are present in a host cell. Examples of such nucleic acid segments are those shown for the herpes virus, HSV-1 in FIG. 1A designated as A–Z of the present specification. These nucleic acid segments may be operably linked to the non-herpes derived components in plasmids A–Z or their functional equivalents. These components may include promoters such as those capable of controlling the herpes α4, the ICP35 genes or their functional equivalent. The recombinant expression vectors may comprise as a promoter either a eukaryotic or prokaryotic promoter, and may include a polyadenylation signal at position 3' of the carboxyl terminal amino acid. The promoter may be within a transcriptional unit of the encoded protein. Vectors may also include markers which have been used for the analysis presented herein. Examples of host cells are BHK cells, Vero, *E. coli* or other eukaryotic or prokaryotic cells known to those of skill in the art to permit expression of transferred vectors according to the present invention.

This invention further relates to methods of preparing a herpes protease. An embodiment of such methods includes the following steps:

(1) Preparing a nucleic acid segment which encodes the herpes protease; and (2) Allowing the segment to be expressed in order to produce the protein.

In an illustrative embodiment the method of preparing a protease includes use of a host cell into which the nucleic acid segment has been transferred. The host cell is cultured under conditions suitable for expression and the protein is thereby expressed. The method may also include a step wherein the protein is isolated and purified by methods well known to those skilled in the art. The degree of purification required will depend on the application for which the protein is intended. Alternatively, the nucleic acid segment may be expressed in a cell free system, such as a rabbit reticulocyte lysate, or synthesized by an automated protein synthesizer as referenced herein.

A nucleic acid segment which codes for the herpes protease or for the ICP35 proteins may be prepared by obtaining viral genomic DNA from cells which are infected with herpes, applying the proteolytic site containing nucleic acid sequence region within the nucleic acid of interest, and preparing recombinant clones which include such amplified nucleic acid sequences. The clones may be then selected to contain the desired amplified nucleic acid segments by employing monoclonal antibodies directed to at least the region coding for the proteolytic domain of the protease or the cleavage site of the ICP35 protein to screen such clones. Other cloning and clone screening techniques well known to those of skill in the art are also suitable (Maniatis).

This invention also relates to a method for cleaving a herpes molecule which includes the steps of treating the molecule with the protease under conditions effective for cleavage. Such conditions are those in which serine proteases generally operate.

In an exemplary embodiment, methods for detecting the herpes protease in tissue samples consist of preparing antibodies directed against the protease, labelling these antibodies, contacting tissue samples with the labelled antibody, and detecting the labelled antibody protein heteroconjugate by standard techniques well known to those of skill in the art. These labels may be fluorescent labels or radioactive labels.

One of the methods for detecting the nucleic acid segments in biological samples is to prepare a nucleotide probe that is capable of hybridizing to a nucleic acid segment substantially as set forth in FIG. 1A, either line 5 or 6, or as disclosed in other areas of the specification herein as coding for a herpes protease or the ICP35 proteins. The nucleotide probe may be labelled. The probe is then incubated with the biological sample to be tested, under selective conditions appropriate for the formation of specific hybrids. The specific hybrids formed between the probes and the nucleic acids of the biological sample are then detected by a variety of methods well known by those skilled in the art, for example, by detecting a radioactive label on the probe. The formation of such hybrids is indicative of the presence of the nucleic acid segment that was sought initially.

A method for treatment of viral infections makes use of the target proteases disclosed herein which are vital to the viral life cycle. An example of such a method comprises preparing an effective mount of an inhibitor of the protease. The amount will depend on the route of treatment. The route may be topical creams, ointments or sprays applied directly to the skin, or intravenous injection for systemic infections. The inhibitor is contemplated to be combined with a pharmacologically acceptable carrier would be appropriate for use in humans depending on the route of application. Finally a therapeutic amount of the inhibitor is determined such that the herpes virus itself is inhibited from reproducing, but the host cells are not destroyed. The method of treatment disclosed herein is particularly applicable to the herpes virus simplex subtypes 1 or 2, but will be generally applicable to the herpes family, members of which are known to have extensive DNA homologies.

This inhibition may be either at the level of transcription, translation, or protein action. Interference with transcription would necessitate interference with mRNA formation on a DNA template. Interference with translation would necessitate interfering with the synthesis of proteins on the mRNA template. Alternatively, the action of the protease may itself be disrupted either by destroying the structure of the protease, in particular its proteolytic domain, altering the cleavage site of it substrate, or by providing a false substrate which inactivates the protease. Another form of inhibitor comprises a nucleic acid segment which is capable of hybridizing with the coding sequence of a herpes protease, but forms a hybrid which inhibits transcription of the mRNA from which the protease would be translated.

There are several inhibitors that appear to be suitable for purposes of this invention. It has been found that chymostatin and diisopropyl fluorophosphate provide 100% inhibition of the protease in an in vitro assay. Phenylmethansulfonyl fluoride provides at least 50% inhibition, this reduction is due to the instability of the inhibitor over time. Other contemplated inhibitors include antipain, aprotinin, leupeptin, (4-amino-phenyl)-methane sulfonyl fluoride, and any other serine protease inhibitors that tests positive in the candidate screening assay described herein. In particular embodiments, non-toxic derivatives of the inhibitors disclosed herein are contemplated.

In order to determine still other inhibitors the candidate substances of interest are screened by preparing a virus protease, combining the protease with the candidate inhibitor substance, and selecting a substrate capable of being cleaved by the protease. The assay is conducted by contacting the substrate with the protease-candidate substance combination, and determining whether the candidate substance has inhibited the action of the protease on the substrate. In an illustrative embodiment, the virus protease used to test for a candidate substance is the purified herpes protease synthesized in vitro in a rabbit reticulocyte lysate by methods disclosed in the present specification.

The protease is combined with the candidate inhibitor substance either in a laboratory in vitro assay or in a test organism. The substrate selected which is capable of being cleaved by the protease, may be the protease itself, or at least the cleavage site of the ICP35 protein precursor c, d. After contacting the substrate with a protease and the candidate inhibitor substance it can be determined whether the substance has inhibited the action of the protease on the substrate by determining whether cleavage of the substrate has taken place. In one embodiment this may be determined by seeing if the ICP35 c, d proteins have produced ICP35 subunits e and f as determined by SDS gel electrophoresis, which are only formed by cleavage of c, d by the protease. If the proteins have not been cleaved, the inference is that the candidate substance indeed inhibits the virus protease. This inhibitor may then be used in therapeutic trials.

The virus protease used in the candidate inhibitor substance assay may be prepared through the application of genetic recombinant technology, wherein, for example, an expression vector includes at least the proteolytic module of the protease. The expression vector is then transferred into an appropriate host cell under conditions which permit expression of the coding sequence. After the sequence has been expressed in the form of a protease or protease segment, the protease may be collected from the cell and further purified if required, by methods well known to those of skill in the art.

An alternative method of preparing the herpes protease is to obtain a sample which contains the protease, for example a herpes infected tissue segment or exudate. The sample is then homogenized and fractionated to obtain a protease fraction. The protease fraction may be then further isolated and purified by methods known to those of skill in the art depending upon the particular application.

This invention also relates to a method for selecting a serine protease with functions equivalent to those disclosed herein in different species of herpes, other non-herpes virus or, indeed, any organism. To select the protease, an amino acid sequence comprising at least the cleavage site of the protease disclosed in the present specification is prepared. The candidate viral protease is then contacted with the cleavage site containing the amino acid sequence which is susceptible to cleavage by a viral serine protease. Finally a determination is made whether cleavage has occurred by using the ICP35 substrate and determining whether ICP35 c, d has been altered to e and f. By these methods, it has been shown that the HSV-2 protease is capable of cleaving ICP35 c, d to e and f.

The methods and compositions of the present invention have made it possible to identify essential serine proteases in other species. The methods of the present invention are generally applicable, only the source genome will change. It is expected that these serine proteases are encoded by conservative segments and are widespread. For the herpes viruses, four of the six viral DNA sequences (HSV-1, EBV, VZV, CMV) are reported and have been entered into a computer data base available to those of skill in the art. Homologies in amino acid sequences and function are expected based on the conservative nature of serine proteases, and homologies detected previously among related species, e.g. the herpes family. (Davison et al., 1986; McGeoch et al., 1988) Thus, it is predictable that $U_L26$ of HSV-1, BVRF2 of EBV, $U_L80$ of CMV, Gene 33 of VZV play the same or similar role in the maturation of capsid and encode a protease. Because extensive sequence homology was found between these presumptive proteases and HSV-1 $U_L26$, it is believed that the action or cleavage mechanism of these protease is the same as the HSV-1 $U_L26$. Thus, it is not surprising that the present invention including inhibitor described have against herpes simplex virus (HSV-1 and HSV-2) and can be applicable to the treatment of other herpes viruses (EBV, VZV, CMV and human herpes virus 6).

As an indication that the serine proteases of the present invention will not be confined to the herpes family, there are reports of capsid assembly in other microbes. Bacteriophage $T_4$ and lambda are most commonly studied for capsid assembly. In these phages, first a preformed capsid is assembled by interaction of outer coat protein and inner scaffolding protein. Then, the scaffolding protein is cleaved by a phage-encoded protease and removed from the capsid. At the same time, the phage DNA is packaged into the capsid to give rise to mature capsid. The cleavage of scaffolding protein is essential to produce mature capsid. Recently, cryo-electromicroscopy studies revealed the similarity of the capsid structure between HSV and lambda phage. ICP35 has been proposed to function as a scaffolding protein in the process of HSV capsid maturation. The cleavage of ICP35 by the proteases of the present invention is required for the capsid maturation and is essential for the replication of the virus. The proteases disclosed herein function as a counterpart to those of phages which cleave the ICP 35 protein to initiate DNA packaging. Therefore, the candidate protease inhibitor assays and methods of treatment disclosed herein have wide applicability than to only the herpes family.

DEFINITIONS

Downstream refers to nucleic acid sequences found in a 3' direction from a given point of reference along a nucleic acid molecule.

An epitope is an amino acid sequence which is an antigenic determinant.

An open reading frame (ORF) contains a series of triplets coding for amino acids without any termination codons. Sequences of this type are potentially translatable into a protein.

Substantially purified in reference to DNA refers to DNA segments isolated free of their natural state as they may be present in the genome of an organism, and is intended to include segments as they would exist upon genetic engineering, e.g. by insertion into a recombinant vector.

A transcriptional unit is the distance between sites of initiation and termination by RNA polymerase.

Upstream refers to nucleic acid sequences found in a 5' direction from a given point of reference along a nucleic acid molecule.

A viral protease is an enzyme capable of cleaving viral precursor proteins at a specific site.

BRIEF DESCRIPTION OF DRAWINGS

FIGS. 1A, 1B, 1C, and 1D Sequence arrangement of the HSV-1 genome, the positions of $U_L26$ and $U_L26.5$ open reading frames and their transcripts, and the structure of the test plasmids constructed for use in the present invention. 1B (SEQ ID NO: 1 and SEQ ID NO: 2). Nucleotide and amino acid sequence of the $U_L26$ open reading frame. The +1 site corresponds to the translational initiation site of $U_L26$ open reading frame.

DESCRIPTION OF THE PREFERRED EMBODIMENTS

Figure 2:
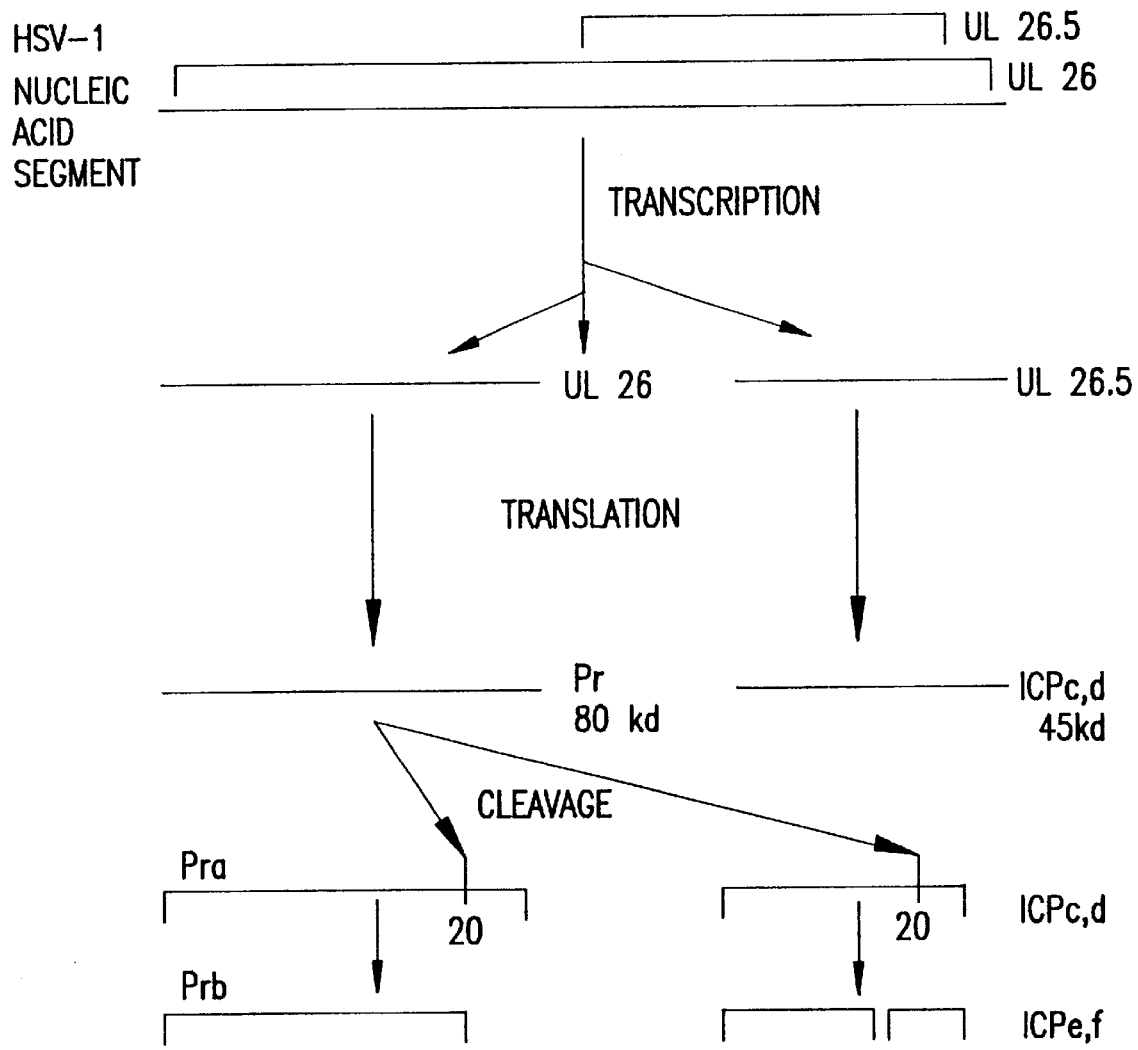
FIG. 2. A schematic representation of the relationship among the HSV-1 genomic DNA, the UL26 and UL26.5 open reading frames (ORF), and the translational and post-translational products of this genetic system.

The present invention relates to herpes proteases and to nucleic acid segments which encode such proteases. The protease encoding segments also contain at least one coding domain for proteins used in capsid production during viral replication. Substrates of the protease include its own amino acid sequence and the precursors of viral capsid proteins. (FIG. 2). Inhibitors of the protease arrest the viral life cycle, thereby offering a means of therapeutic intervention. An illustrative embodiment of the methods and compositions of the present invention, employs HSV-1 as a protease source.

A novel herpes protease has been identified in HSV-1, purified and abbreviated as "Pr." A weapon forged to directly attack virus production is provided by inhibiting the action of the Pr protease. Because the protease is essential for packaging of DNA into the viral capsid, inhibition of the protease disrupts the replication cycle of the virus. Treatment with inhibitors of the protease alleviates clinical effects and reduces risk of transmission.

The herpes protease is a product of a region of the HSV genome, the $U_L26$ SEQ ID NO: 1 open reading frame. The protease is both a necessary and the sole viral protein that suffices to effect its own cleavage and that of the product of the $U_L26.5$ open reading frame (ORF) a region identified and purified as an aspect of the present invention. The product of the $U_L26$ ORF, a protein that has been designated as Pra in the present invention, is a previously undescribed herpes protease, the first protease ever purified from the herpes virus. In cell free systems, Pra cleaved itself to Prb providing evidence that the translation product Pra, can function as a protease. (FIG. 2) Prb, the designation assigned to the product of the autocatalytic cleavage of Pra, is approximately 20 amino acids smaller than Pra.

Characteristics of the protease of the present invention are not only that it catalyzes its own cleavage, but surprisingly, a second substrate on which it acts, the more abundant substrate, is encoded by a sequence entirely contained within the gene encoding the protease. The protease and the second substrate share amino acid sequences at their carboxyl termini. A surprising and unexpected finding was that the coding segment for the second substrate codes for viral capsid proteins designated ICP35, and is a newly identified gene designated $U_L26.5$.

The expression of the $U_L26$ gene in the form of a protease is essential for viral maturation. The evidence for this statement is that a temperature-sensitive mutation reported by Preston, et al. (1983) at the $U_L26$ open reading frame has a lethal effect on capsid maturation.

One of the reasons these proteases were successfully isolated and purified, was because of the choice of a key test substrate, the ICP35 proteins. To delve into the morass of genetic complexity that is the herpes genome, another productive step was that a large number of plasmids were constructed, each with a specific construction strategy designed to answer a specific question about the mechanism of herpes genetic pathways. Into some of the plasmids, a marker sequence was inserted to permit tracing of the paths of genetic action. The markers in a series of plasmid constructs included deletions or insertions of an α4 promoter or of a sequence encoding a cytomegalovirus epitope capable of reacting with a mouse monoclonal antibody. These constructs revealed dramatic and surprising differences in the genetic action of a region of the herpes genome from that predicted from previous work on the structure and action of the $U_L26$ ORF.

In previous work, McGeoch et al. (1988) predicted that the $U_L26$ frame encodes ICP35. The product of $U_L26$ predicted from the nucleotide sequences in that open reading frame, however, turned out to be considerably larger than ICP35. A hierarchical genetic complexity was revealed as responsible for production of the herpes capsid protein. What is disclosed in the present invention is a dissection of the domain designated $U_L26$ into two overlapping transcriptional units yielding proteins which share part of an amino acid sequence. What had previously been designated ICP35 turns out to be encoded only by a portion of the $U_L26$ open reading frame. For purposes of the present invention, that unit has been designated $U_L26.5$.

By methods disclosed herein, the herpes virus has been forced to divulge some of its inner secrets. Three basic techniques were employed: 1. transfecting cells with test plasmids and then infecting them with herpes; 2. transfecting cells with two plasmids; 3. in vitro translation. Two overlapping nucleic acid sequences, which comprise two genes (independent transcription units), have been ferreted out of the herpes simplex virus 1 (HSV-1). The larger of the sequences is designated $U_L26$ and encodes a protein of an apparent molecular weight of approximately 75–85 kd as determined by SDS-PAGE. This protein is a serine protease which is capable of processing itself and the ICP35 protein precursors by carboxyl-terminal proteolytic cleavage. The smaller sequence is designated $U_L26.5$ and encodes a protein of an apparent molecular weight of approximately 35–50 kd as determined by SDS-PAGE. Both genes have been cloned.

The protease of the present invention has general applicability. Homologs of the substrate of the Pra protease, which cleaves a precursor to form the ICP35 proteins, have been detected in other herpes viruses. It is likely, therefore, that the methods of the present invention will reveal the protease in other members of the virus family, and in other species. As one example, it has been reported recently that the CMV equivalent of the ICP35 protein is cleaved at the carboxyl terminus (Gibson et al., 1990, Schenk et al. 1991), although the CMV protease has not been identified as yet in that species. The herpes-cleaved protease is, therefore, likely to affect cleavage in to other herpes viruses.

The existence of a homologous open reading frame to ICP35 in the Varicella-Zoster Virus (VZV) genome (Davison and Scott, 1986; Davison and McGeoch, 1986) suggests that the ICP35 equivalent and the corresponding protease are conserved among the various herpes viruses. Because the amino acid sequence of ICP35 is entirely contained in the carboxyl terminus of Pr and because ICP35 does not show demonstrable proteolytic activity, it is expected that the proteolytic activity exhibited by Pr is expressed by the amino terminal domain of the protein. It is of interest to note that in the VZV genome (Davison and Scott, 1986), the open reading frame corresponding to $U_L26$ exhibits greater homology in amino acid sequence at the amino terminus rather than at the carboxyl terminus.

Manipulation of the Herpes Simplex Virus (HSV) Genome

The importance of a viral protease as a therapeutic target is clear from a consideration of viral replication mechanisms. The herpes simplex virus has a genome comprising a linear, double-stranded DNA molecule (molecular weight approximately $100 \times 10^6$) large enough to encode $7^3$ different gene products. The structure of the genome is unusual among DNA viruses in that two unique nucleotide sequences are flanked by inverted repeated sequences.

The viral genome is packaged within a regular icosahedral protein shell (capsid) composed of 162 capsomes. The outer covering of the virus is a lipid containing membrane envelope derived from modified cell membrane. Cell proteins are not detected in the virion envelope. Glycoproteins in the lipid bilayer of the envelope mediate attachment of virus to the host cell, surface, and penetration of virus into the cell and viral maturation and egress. A tegument exists between the capsid and the lipid bilayer. Within the capsid are DNA polyamins, and DNA-binding proteins.

Clinical problems result when infection of cells is followed by replication and spread of the virus. After the viral genome reaches the nucleus of the cell, expression of viral genes occurs in a highly regulated fashion. Cell death may result from viral infection and replication. Protease inhibition will block replication. In vivo infections of certain cells, in particular sensory neurons, does not necessarily result in replication of virus and cell death. A latent phase may occur.

Figure 1A:
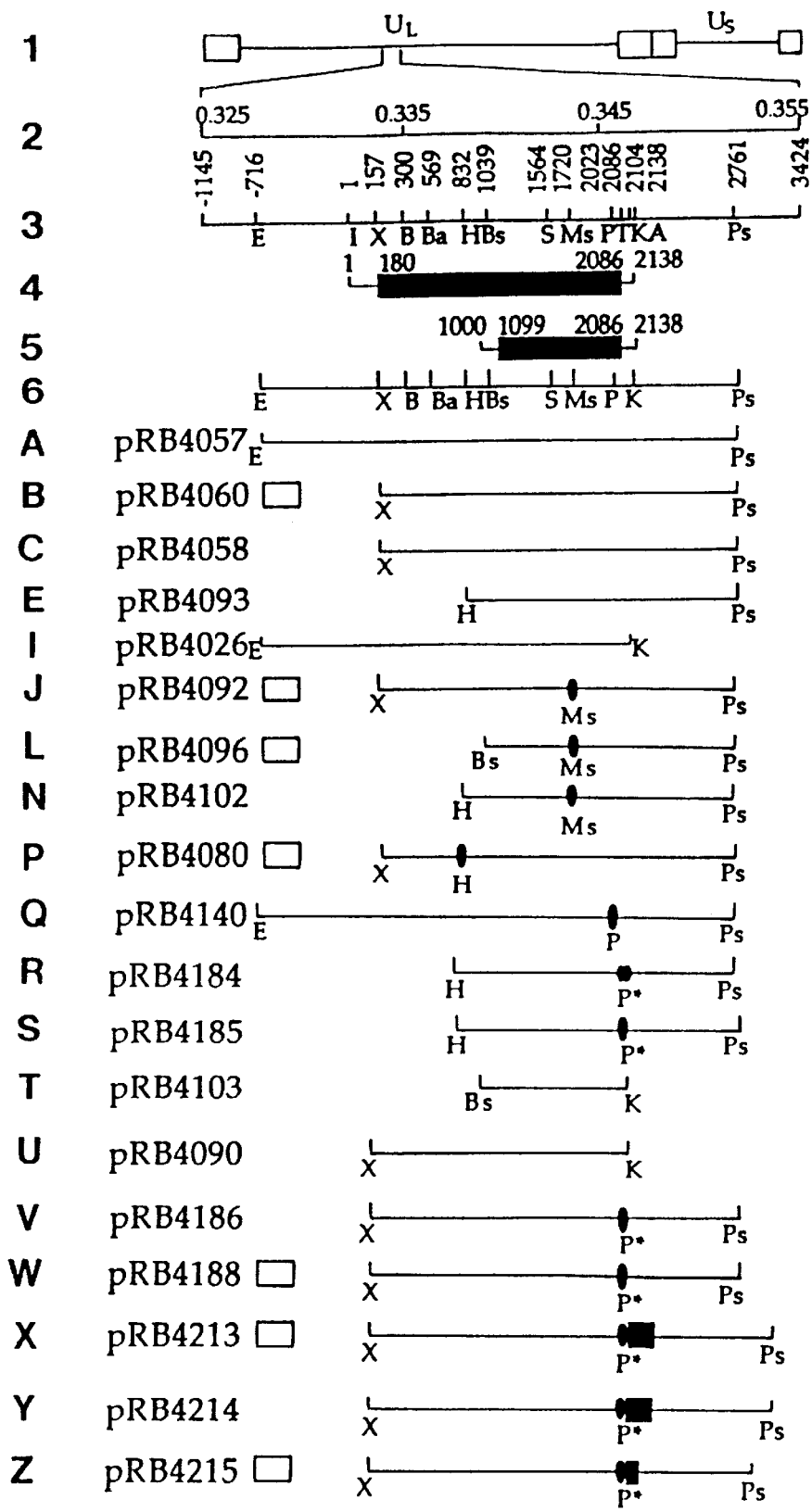

Sequence arrangement of HSV-1 genome, the positions of $U_L26$ and $U_L26.5$ open reading frames and their transcripts and the structure of the test plasmids constructed for these studies are shown in FIG. 1A.

Line 1,—schematic representation of the sequence arrangement of HSV-1 genome. $U_L$ and $U_S$ refer to the long unique and short unique sequences flanked by terminal inverted repeats shown as rectangles.

Lines 2 and 3,—genome map position, nucleotide numbers relative to the approximate transcription initiation site of $U_L26$ indicated by letter I at +1, and restriction endonuclease sites of the HSV-1 EcoRI-PstI DNA fragment. This line also shows the position of the translational termination codon(T) and of the single poly(A) signal (A) which serve both the $U_L26$ and $U_L26.5$ RNAs.

Line 4, Locations of the methionine codons contained in the $U_L26$ ORF.

Lines 5 and 6,—the filled rectangles represent the coding domains of the $U_L26$ and $U_L26.5$ open reading frames. The numbers refer to the positions of the transcription initiation site, the translation initiation and termination codons and of the poly(A) signal for both open reading frames relate to nucleotide +1 of $U_L26$.

Line 7 is a restriction endonuclease map drawn to scale with reference to lines A through Z which are schematic representations of the HSV-1 sequences contained in the plasmid constructs used in the studies described in this report. The construction of the plasmids shown schematically in lines A through Z is described in Example 1. The source of the α4 promotor (open rectangle) shown in plasmids B, D, H, J, K, L, M, P, W, X, and Z was BamHI Z DNA fragment (Post et al, 1981) inserted in proper transcriptional orientation. The CMV epitope is shown as a filled oval. The oligonucleotide C with its complement is shown as a filled rectangle and the new created PmlI site is marked as P+. The restriction endonuclease sites were abbreviated as follows: B, BamHI; Ba, BalI; Bs, BstEII; E, EcoNI; H, HpaI; K, KpnI; Ms, MstII; P, PmlI; Ps, PstI; S, SalI; X, XmaI.

In order to identify the in vitro translation of $U_L26$ and $U_L26.5$ the unprocessed species of ICP35, open reading frames, both the $U_L26$ and $U_L26.5$ open reading frames were cloned into PGEM3Z-f(+) to derive plasmids T and U, respectively (FIG. 1A). RNAs corresponding to the mRNAs of $U_L26$ and $U_L26.5$ were transcribed by Sp6RNA polymerase and translated in nuclease-treated rabbit reticulocyte lysates. The results indicated that $U_L26$ and $U_L26.5$ specify proteins each of which form double bands with apparent molecular weights of 80 kd (Pra) and 45 kd (ICP35d, c), respectively. The two species of $U_L26.5$ (ICP35) protein synthesized in vitro were found to comigrate with ICP35c, d synthesized in vitro in HSV-1(F) infected cells. It was further found that the unprocessed forms of $U_L26.5$, that is ICP35c, and d, can be processed into ICP35e and f.

It was possible to map (localize) and purify the DNA sequences in the viral genome required for the processing of ICP35c, d into ICP35e, f. BHK cells were transfected with a series of plasmids containing different lengths of HSV-1 DNA sequences, each containing an intact ICP35 gene and superinfected with HSV-1(F) at 39° C. BHK cells transfected with the plasmid A containing the intact $U_L26$ gene (FIG. 1A) generated ICP35e, f in addition to ICP35c, d whereas cells transfected with plasmid C in which the promoter region of $U_L26$ gene was deleted, and only the coding sequence of $U_L26$ was included (FIG. 1A), generated only the unprocessed ICP35c, d. These results suggested that the gene product of $U_L26$ was required for the processing of ICP35, c, d into e, f.

The product of the gene $U_L26$ was found capable of cleaving ICP35c, d into e, f when present in the trans position. To determine whether $U_L26$ acts in trans or in cis, BHK cells were transfected with plasmid N as the substrate for processing and a series of plasmids containing deletions in the $U_L26$ open reading frame, and then infected with HSV-1(F) and maintained at 39° C. The results showed the following:

(i) ICP35c, d did not autocatalyze their own processing into ICP35e, f, inasmuch as the lysates of cells co-transfected with plasmids N and E (FIG. 1A) did not contain ICP35 forms e and f reactive with the CMV monoclonal antibody.

(ii) ICP35C, d were not processed in BHK cells co-transfected with plasmids N and C or I. Plasmids C and I contain deletions in the promoter region and at the polyadenylation site of the $U_L26$ open reading frame, respectively (FIG. 1A).

(iii) ICP35c, d were processed into e, f in BHK cells co-transfected with plasmids N and A or B. Plasmids A and B contain the intact $U_L26$ promoter and open reading frame and the $U_L26$ coding sequence driven by the α4 promoter, respectively. The α-transducing factor in HSV-1(F) induces the α4 promoter to a high level (Post et al., 1981; Battreson and Roizman, 1983) at 39° C. The high level of expression of $U_L26$ may explain the presence of the processed forms of ICP35 (forms e and f) in lysates of cells co-transfected with plasmids N and B.

The importance of the protease encoded by $U_L26$ is indicated by the results showing it to be competent for the processing of ICP35c, d into e, f. It is shown that $U_L26$ and processing of ICP35d, d to e, f are both essential for capsid production because a mutation in that region (in the 5' end of the $U_L26$ ORF) was reported as lethal. (Preston, et al., 1983).

Even more exciting from the perspective of use of the protease as a target for attack on herpes infections is that the protease appears to be the sole protein required for processing of ICP35c, d into e, f proteins required for capsid production. That indicates the protease is essential for capsid formation. To determine whether $U_L26$ is the only viral protein required for this processing and to exclude the possibility that viral genes expressed by the HSV-1(F) genome at 39° C. contribute to the catalysis of ICP35, BIHK cells were co-transfected with a constant amount of plasmid L and different amounts of plasmid B as the genes encoding the substrate and the enzyme for the processing, respectively. In plasmid L (FIG. 1A) the $U_L26.5$ open reading frame was regulated by the α4 promoter and the CMV epitope was inserted at the MstII restriction endonuclease site whereas plasmid B contained the intact $U_L26$ open reading frame driven by the same promoter. Because the α4 is a strong eukaryotic promoter constitutively expressed in transfected cells (Post et al., 1981; Kristie and Roizman, 1984), expression of the $U_L26.5$ and $U_L26$ proteins in cells transfected with plasmid L and B did not require superinfection with HSV-1(F). The results were as follows:

(i) In the absence of viral infection, ICP35c and d were the only two species expressed in cells transfected with plasmid L. The epitopically marked ICP35 expressed by plasmid L was fully processed in cells superinfected with HSV-1(F) at permissive temperature. As expected plasmid B did not produce products reactive with anti CMV antibody.

(ii) In the presence of plasmid B containing $U_L26$, the epitopically marked ICP35c, d expressed by plasmid L were processed into ICP35e, f. At low concentrations of plasmid B, the extent of accumulation of ICP35e, f was directly proportional to the amount of $U_L26$ plasmid DNA co-transfected with plasmid L into BHK cells. The decrease in the amounts of ICP35e, f observed in the presence of the highest amounts of plasmid B may reflect competition between the two plasmids or reduced yield as a result of the toxicity used by high amounts of DNA.

From results of these studies it was concluded that the product of the $U_L26$ is the only viral factor both competent and sufficient to process ICP35c, d into ICP35e, f. The protease is, therefore, essential for capsid development, which in turn is essential for the herpes virus replication life cycle.

The active agents of such medicants include an inhibitor of the protease. The inhibitor may act to countermand the proteolytic action of an already available protease, or to disrupt or prevent the initiation of the translation or transcription of the nucleic acid segments responsible for protease production. The inhibitor may be in the form of a chemical composition, in which case it must be combined with a composition which effects cell incorporation.

If the inhibitor is in the form of nucleic acid segment, it may be incorporated into infected cells by any of the variety of methods well known to those of skill in the art. Those methods are disclosed herein and comprise transfection of a recombinant vector, electroporation, or use of a "gene gun" to force mechanically accelerated nucleic acid particles into infected cells.

EXAMPLE 1

Construction of Plasmids and Their Relation to the HSV Genome

The tools used to mold the genomic clay into useful forms included a set of plasmids cleverly constructed to contain segments of nucleic acid sequences that could be manipulated to identify sections of the nucleic acid sequence of the HSV genome which control production of specific polypeptides, and to isolate those segments and purify their products.

These ingenuous tools were created to identify and manipulate nucleic acid sequences involved in viral infections. In some plasmids, markers were inserted at specific locations in order to trace the products of cleavage, to define nucleotide sequences used for various infective processes. The CMV epitope is shown as a filled oval. The oligonucleotide C with its complement is shown as a filled rectangle. The newly created PmlI site is marked P*. The restriction endonuclease sites are abbreviated as follows: B, BamHI; Ba, BalI; Bs, BstEII; E, EcoNI; H, HpaI; K, KpnI; Ms, MstII; P, PmlI; Ps, PstI; S, SalI; X, XmaI.

Collectively, the HSV-1 sequences carried in plasmids A to Z contain deletions which encompass the entire domain of the $U_L26$ open reading frame. In some instances, e.g. plasmid constructs B and D the promoter of the α4 gene was juxtaposed in the form of the BamHI Z fragment to force a higher level of transcription.

Plasmid constructs designated J through N in FIG. 1A carry in the HSV DNA's a sequence encoding a CMV epitope inserted into the unique MstII site of these fragments. In all but one plasmid construct the BamHI Z fragment was also inserted to augment transcription by the α4 promoter contained in this fragment. The exception was plasmid construct N.

In plasmid O and P the CMV epitope was inserted into the unique HpaI site and only the P plasmid contains the α4 promoter in the form of the BamHI Z fragment.

The following plasmids were constructed: A (pRB4057), B (pRB4060), C (pRB4058), D (pRB4089), E (pRB4093), F (pRB4056), G (pRB4087), H (pRB4088), I (PRB4026), J (pRB4092), K (pRB4094), L (pRB4096), M (pRB4095), N (pRB4102), O (pRB4079) and P (pRB4080), Q (pRB4140), R (pRB4184), S (pRB4185), T (pRB4103), U (pRB4090), V (pRB4186), W (pRB4188), X (pRB4213), Y (pRB4214), Z (pRB4215). pRB4026 was constructed by insertion of the HSV-1 fragment into the KpnI site of pUC18. pRB4057 contains the entire encoding sequence of the $U_L26$ open reading frame, extending 3' from nucleotide –900 relative to the translation initiation site of the gene to approximately 650 nucleotides downstream from its polyadenylation site. pRB4060 was constructed by replacing the viral DNA sequence 23 bp upstream from the translation initiation site of the $U_L26$ open reading frame in pRB4057 with the HSV-1 DNA BamHI Z fragment. The BamHI Z fragment contains at one terminus portions of the 5' transcribed noncoding sequences of the alpah4 gene starting with nucleotide +33 and the upstream untranscribed domains of this gene. The BamHI Z fragment was inserted in the orientation that would juxtapose the α4 promoter in the proper transcriptional orientation to the intact and truncated domains of the $U_L26$ open reading frame. pRB4056, pRB4058, pRB4087, and pRB4093 were derived from pRb4057, and pRB4088 and pRB4089 were derived from pRB4060 by generating deletions by the subcloning techniques described by Sambrook et al. (1989).

Two pairs of oligonucleotides, i.e., oligonucleotide A (5'-AAGGGACAGAAGCCCAACCTGCTAGACCGACTG CGACACCGCAAAAACGGGTACCGACAC-3') with its complement, oligonucleotide B (5'-AAAGGGACAGAAGCCCAACCTGCIAGACCGACT GCGACACCGCAAAAACGGGTACCGACACGA-3') with its complement, and oligonucleotide C (5'-TCGACGTTGACACGGCCCGCGCCGCCGAITTCTT CGTCTCTCAGATGATGGGGGCCCGCCACGTGTGA-3'), were synthesized in Applied Biosystems DNA Synthesizer 380A (Foster City, Calif.). Oligonucleotides A,B and their complements encode the epitope of the CH28-2 monoclonal antibody and contain a KpnI site at the 3' end for convenient screening of the oligonucleotide insertion in plasmids. pRB4079 and pRB4080 were derived by inserting the oligonucleotide A sequence into the unique HpaI site of pRB4057 and pRB4060 respectively. pRB4092 was derived by inserting the oligonucleotide B sequence into the unique MstII site of pRB4060. pRB4094, pRB4095, pRB4096, and pRB4102 were derived from pRB4092 by generating deletions by means of common subcloning techniques (Sambrook, et al., 1989). All insertion sites of these plasmids were sequenced to verify that the CMV epitope was inserted in the same frame as the $U_L26$ open reading frame.

Plasmid Q (pRB4140) was derived by inserting oligonucleotide A with its complement into the unique PmlI site of plasmid A The sequence encodes the authentic $U_L26$ sequence from the PmlI site to the translation termination site but with the addition of a new PmlI site of the $U_L26$ open reading frame in the proper orientation resulted in the creation of a new PmlI site between the carboxyl terminal amino acid and the stop codon of the $U_L26$ open reading frame. In addition, the sequence 'GTG' at the authentic PmlL site has been changed to sequence 'GTC'. By insertion of the sequence C into the unique PmlL site of the $U_L26$ open reading from the proper orientation resulted in the creation of a new PmlI site between the carboxyl terminal amino acid and the stop codon of $U_L26$. The original, authentic PmlI site was destroyed without changing the $U_L26$ amino acid sequence because the codon "GTG" and "GTC" encode the same amino acid. Therefore, the net effect of the insertion of oligonucleotide C with its complement to $U_L26$ open reading frame was that $U_L26$ had two additional amino acids between its authentic carboxyl terminal amino acid and its stop codon which were encoded by the new created PmlI recognition sequence. Plasmid R (pRB4184) was derived by inserting sequence C into the PmlL site of plasmids E (pRB4093), and S (pRB4185) was derived by inserting the oligonucleotide A with its complement into the PmlL site of plasmid R Plasmids T, U, V and W (pRB4103, pRN4090, pRB4186 and pRB4188) were derived from plasmids B and S by subcloning. Plasmids X, Y and Z (pRB4213, pRB4214, and pRB4215) were constructed by inserting in frame into the $U_L26$ open reading frame at the site between the 3' end of the CMV sequence and the stop codon, either a sequence encoding 256 amino acids comprising five homologs of IgG binding domains of the staphylococcal protein A or a sequence encoding 129 amino acids and comprising two such domains. These sequences were the BclL-HincII fragment and HindIII-HincII fragment of the protein A gene fusion vector pRIT5 (Pharmacia, Piscataway, N.J.), respectively. The vector for plasmids T, U, V, and Y was derived from PGEM3Zf(+) (Promega, Madison, Wis.) and these plasmids could be used as templates for in vitro transcription by T7 or Sp6 RNA polymerases. The vectors for all other plasmids were derived from pUC18 (New England Biolabs, Mass.) All the insertion sites of the oligonucleotide sequences A and C with their complement into the plasmids were sequenced to verify that the CMV epitope and the amino acid sequence encoded by oligonucleotide C with their complement were inserted in frame with the $U_L26$ open reading frame.

A restriction endonuclease map is drawn to scale on-line 9 with reference to lines A through Z which are schematic representations of the HSV-1 sequences contained in the plasmid constructs used in the studies described herein.

EXAMPLE 2
Use of the Plasmids to Isolate and Purify Viral Components

Host cells were transfected with the plasmid constructs of FIG. 1A or protein can be synthesized in vitro from rabbit reticulocyte lysate systems with the plasmids. Photographs of polypeptides from cells that were transfected with the plasmid constructs and superinfected with virus, taken after the electrophoretic separation in polyacrylamide gels, electrical transferring to a nitrocellulose sheet, and reaction with goat anti-mouse immunoglobulin antibody coupled to peroxidase, were used to analyze the nucleic acid sequences responsible for the mechanisms of infection. Experimental details of the polypeptide purification are described in the Materials and Methods.

EXAMPLE 3
Analysis of Transcriptional Units

The nucleotide sequence (SEQ ID NO: 1) of $U_L26$ surprisingly and unexpectedly were found to be contained in two transcriptional units. Two probes were constructed to map the transcripts of $U_L26$. Probe 1, designed to identify the 5' terminus of the $U_L26$ in RNA, consisted of the EcoNI-BamH1 fragment labelled at the BamHI site whereas probe 2 consisted of the XcmI-BstEII fragment labelled at the BstEII site (FIG. 1).

Figure 3:
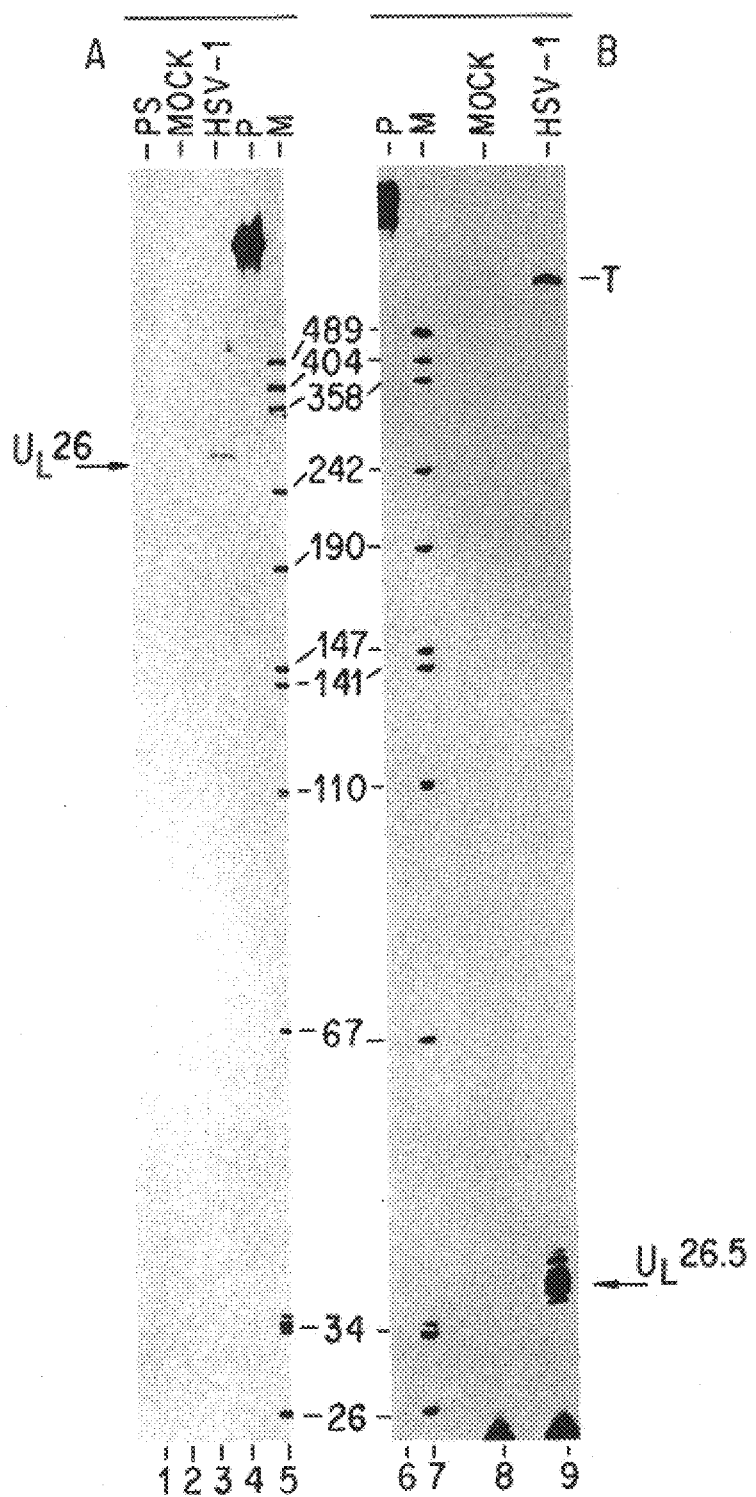
FIG. 3. Autoradiographic image of DNA probe 1 (A) and probe 2 (B) hybridized to total cytoplasmic RNA from mock-infected and 12-hr-infected Vero cells and digested with S1 nuclease.

An autoradiographic image of DNA probe 1 (A) and probe 2 (B) hybridized to total cytoplasmic RNA from mock-infected and 12-h-infected Vero cells and digested with S1 nuclease, is presented in FIG. 3. The RNAs were prepared as described in the Materials and Methods herein. In FIG. 3, lane 1 (PS), an S1-digested probe 1 appears as it is under the same conditions of hybridization and digestion as those shown in lanes MOCK and HSV-1.

Lanes 2 and 8 (MOCK), shows RNA extracted from cells 12 h after mock infection Lanes 3 and 9 (HSV-1), shows RNA extracted from cells infected with HSV-1(F) and maintained for 12 h.

Lanes 4 and 7 (P), indicate positions of the undigested probes (probe 1 or 2).

Lanes 5 and 7 (M), present 5' end-labeled fragments obtained from digestion of PGEM3Z DNA with the enzyme MspI.

Arrows in FIG. 3 indicate the protected 5' termini of $U_L26$(A) and $U_L26.5$(B) RNAs. T, Position of the HSV-1 sequences in probe 2 protected by the $U_L26$ RNA.

The results of the S1 analyses illustrated in FIG. 3 are that cytoplasmic RNA hybridized to probe 1 protected a fragment approximately 300 nucleotides long(lane 3).

Nucleotide 300 upstream from the BamH1 site was designated as +1 of UL26. The first methionine codon after the approximate transcription initiation site is at position +180.

Cytoplasmic RNA hybridized to probe 2 yielded two sets of fragments protected from S1 digestion(lane 9). The first fragment contained all of the HSV-1 DNA sequences(band T). The second set of protected fragments formed several bands ranging from 35–40 nucleotides in length(lane 2, band UL 26.5). Thus, the transcription initiation site of this transcript was approximately at nucleotide +1000 relative to nucleotide +1 of UL26. The first methionine codon downstream from the transcription initiation site of this RNA was at position +1099. The longer RNA was designated $U_L26$.

EXAMPLE 4
Location and Isolation of the ICP 35 Gene

In order to localize the position of the coding domain of the gene specifying ICP35, a series of deletions in open reading frame $U_L26$ were tested for their capacity to express ICP35.

Figure 4:
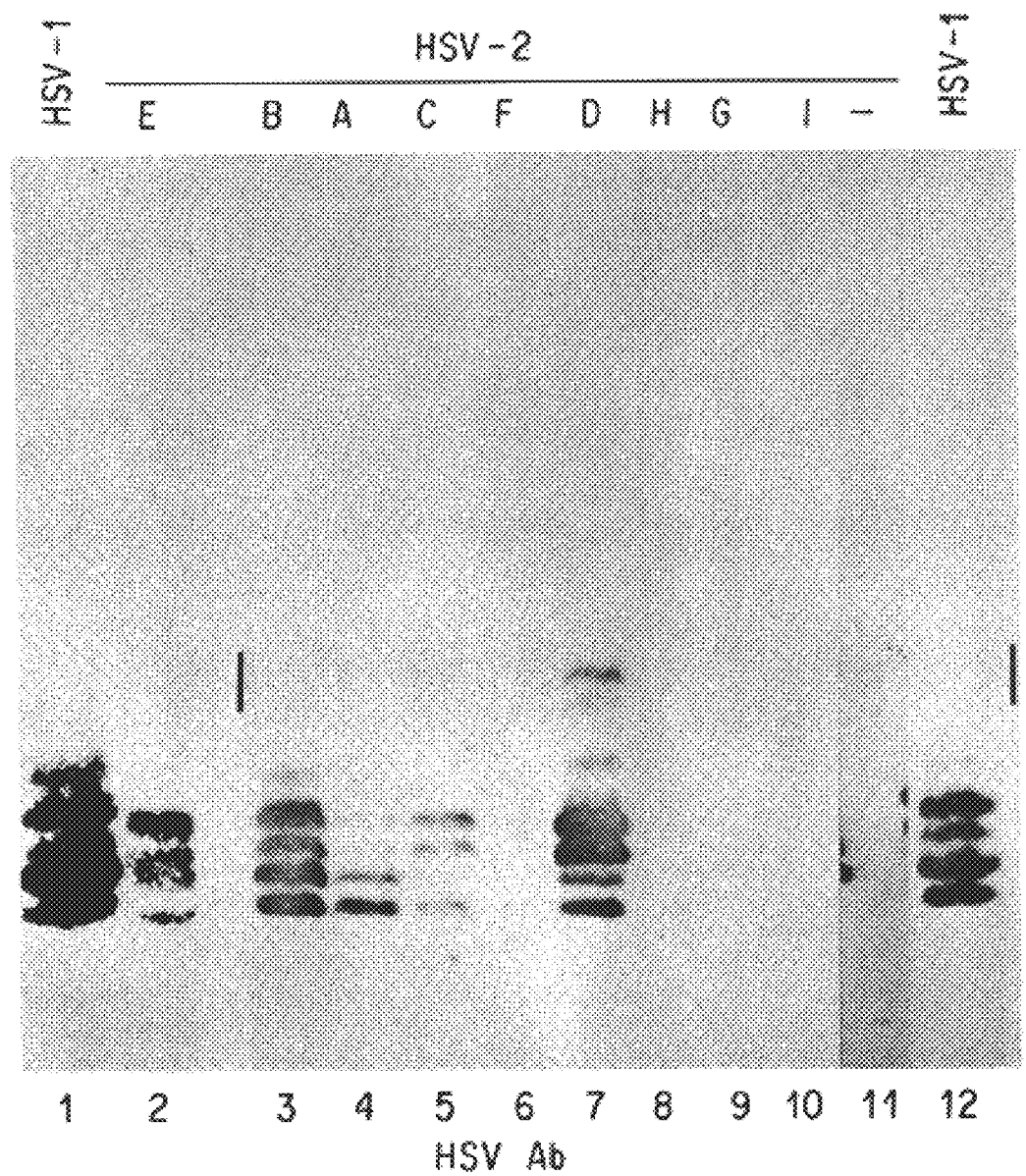
FIG. 4. Photograph of polypeptides from cells transfected with plasmid constructs and superinfected with virus, electrophoretically separated in polyacrylamide gels, electrically transferred to a nitrocellulose sheet, reacted with goat monoclonal antibody H725 (HSV Ab) against HSV-1 ICP35.

BHK cells were transfected with plasmid constructs O, N and P (FIG. 1A) then infected with HSV-2 (FIG. 4). The letters across the top of the gel shown in FIG. 4 identify the plasmid constructs with which the cells were transfected. A dash or the absence of a letter indicates that the cells were infected but not transfected. The vertical lines identify the slow-migrating bands. The shortest fragment which yielded HSV-1 ICP35 was plasmid E(lane 2). Because this plasmid construct was expressed from its endogenous promoter, the results indicate that the sequences contained in the HpaI-PstI fragment contain both the coding sequences and the promoter of the gene encoding ICP35. Plasmid E contains all of the sequences of UL26.5 RNA plus 168 nucleotides.

EXAMPLE 5
Open Reading Frame Isolation and Characterization

Figure 5:
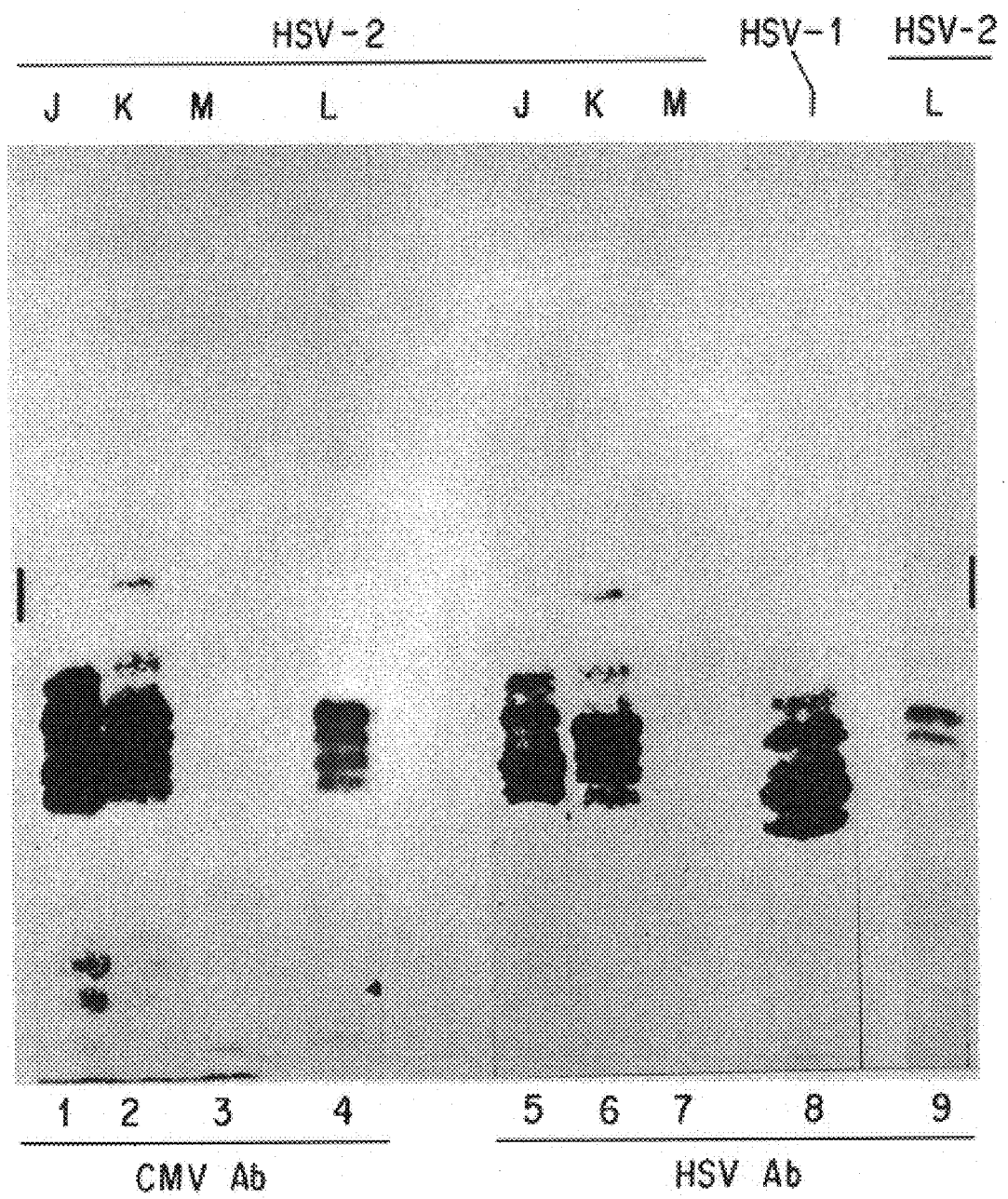
FIG. 5. Photograph of polypeptides from cells transfected with plasmid constructs and superinfected with virus, electrophoretically separated in polyacrylamide gels, electrically transferred to nitrocellulose sheets, and reacted with monoclonal antibody H725 (HSV Ab) or CH28-2 (CMV Ab).

In FIG. 5, a photograph of polypeptides extracted from cells transfected with plasmid constructs and superinfected with virus, was taken after electrophoretical separation in polyacrylamide gels, electrical transferring to nitrocellulose sheets, and reacting with monoclonal antibody H725 (HSV Ab) or CH28-2 (CMV Ab). The letters across the top of the gel identify the plasmid constructs with which the cells were transfected. A dash or the absence of a letter indicates that the cells were infected but not transfected. The vertical lines identify the slow-migrating bands.

FIG. 5 shows that BHK cells transfected with construct J,K, or L made a family of proteins which reacted with both anti-HSV-1 ICP35(H725) and anti-CMV(CH28-2) monoclonal antibodies. The formation of the characteristic four ICP35 bands by the products of transfection of plasmid construct L indicates that the initiating methionine codon for ICP35 is at position 1099.

These results indicate that the $U_L26.5$ coding sequences specifying ICP35 constitute a part of and are in frame with, those of $U_L26$. In the preceding section it was shown that ICP35 could be expressed by transactivation of the DNA sequences contained in the HpaI-PstI fragment. Because plasmid construct E could be transactivated by HSV-2, it may also be concluded that the coding sequences of UL26 include both the coding sequences and the promoter domain of the gene specifying ICP35.

EXAMPLE 6
Use of Anti-CMV mAb

Figure 6:
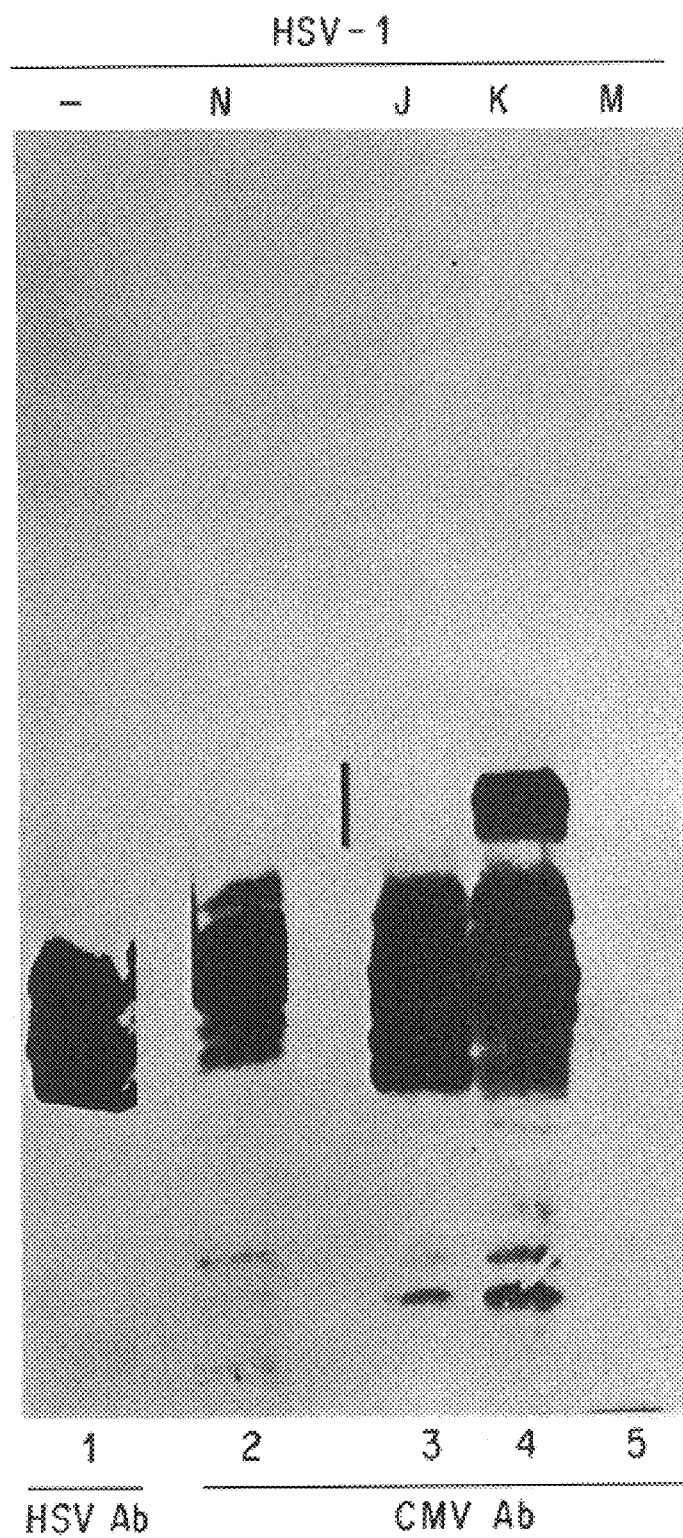
FIG. 6. Photograph of polypeptides from cells transfected with plasmid constructs and superinfected with HSV-1, electrophoretically separated in polyacrylamide gels, electrically transferred to nitrocellulose sheets, and reacted with monoclonal antibody H725 (HSV Ab) or CH28-2 (CMV Ab).

A photograph of polypeptides from cells transfected with plasmid constructs and superinfected with HSV-1, was taken after electrophoretical separation in use of SDS polyacrylamide gels, electrical transferring to nitrocellulose sheets, and reacting with monoclonal antibody H725 (HSV Ab) or CH28-2 (CMV Ab). The letters across the top of the gel shown in FIG. 6 identify the plasmid constructs with which the cells were transfected. A dash or the absence of a letter indicates that the cells were infected but not transfected. The vertical lines identify the slow-migrating bands. These results indicate that use of the anti-CMV monoclonal antibody obviates the need to superinfect the cell with a heterologous virus.

Figure 7:
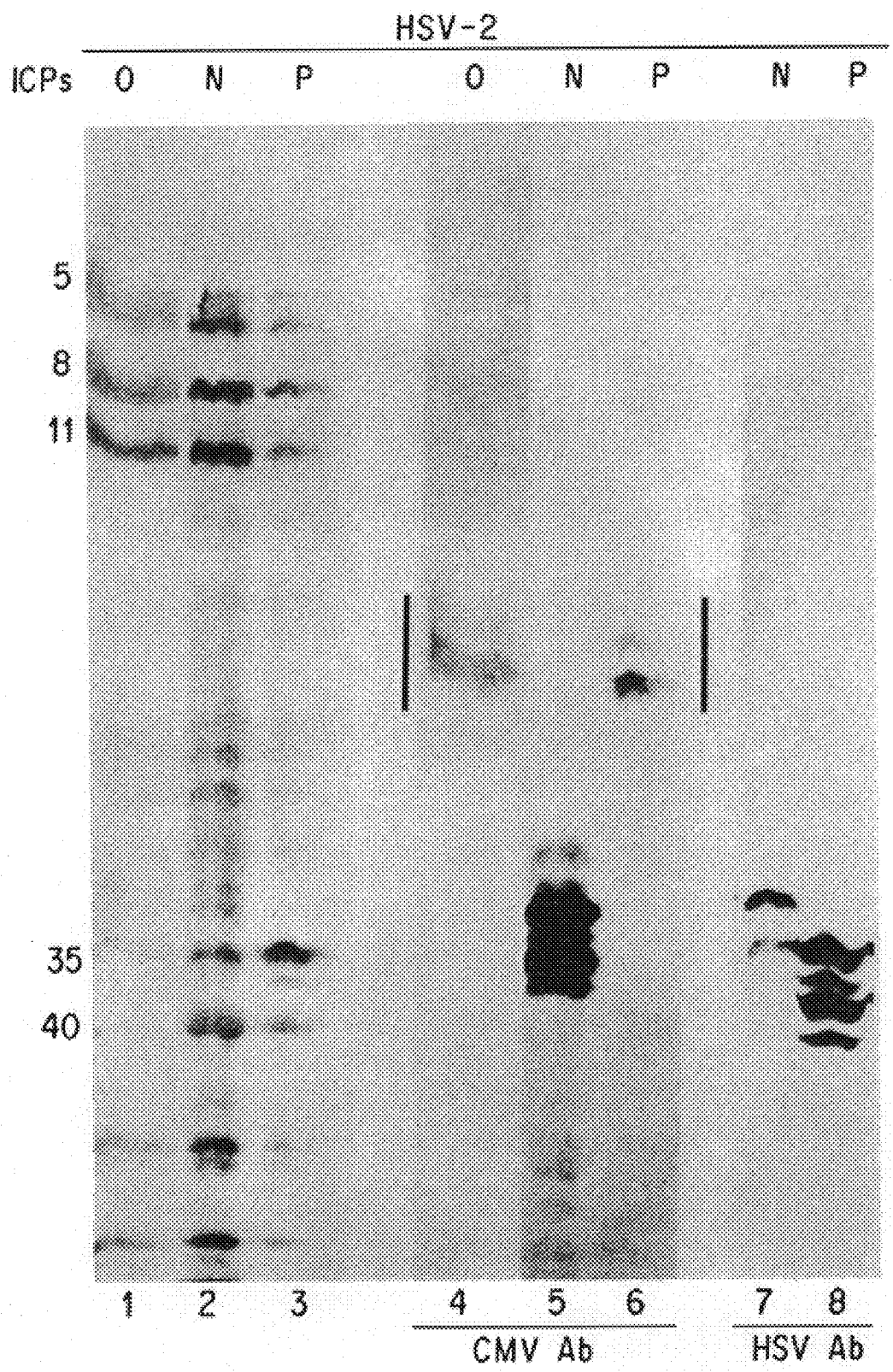
FIG. 7. Autoradiographic images and photograph of polypeptides from cells transfected with plasmid constructs and superinfected with virus, electrophoretically separated in polyacrylamide gels, electrically transferred to mitrocellulose sheets, and reacted with monoclonal antibody H725 (HSV Ab) or CH28-2 (CMV Ab).

EXAMPLE 7
Identification, Isolation and Characterization of the Product of the $U_L26$ ORF FIG. 7 presents autoradiographic images and a photograph of polypeptides from BHK cells transfected with plasmid constructs and superinfected with virus, after the cells were electrophoretically separated in polyacrylamide gels, electrically transferred to nitrocellulose sheets, and reacted with monoclonal antibody H725 (HSV Ab) or CH28-2 (CMV Ab). The letters across the top of the gel identify the plasmid constructs with which the cells were transfected. The vertical line and arrow identify the product of the $U_L26$ protein.

In FIG. 7, lanes 1, 2, and 3 are autoradiographic images of proteins labeled with [$^{35}$S]methionine as described in the Materials and Methods. The infected cell proteins (ICPs) of HSV-2 were numbered according to Morse et al. (1978).

Lanes 8, 9, and 10 show lysates of the same cells as shown in lane 4, 5, and 6 stained with H725 rather than with the CH28-2 monoclonal antibodies.

Lane 7 shows the lysate of cells transfected with plasmid construct J, in which $U_L26$ is driven by the α4 promoter, infected with HSV-1(F) and maintained at 39° C. Under these conditions, only α and a few β proteins are expressed, but the ICP35 of HSV-I(F) is not expressed. The ICP35 in the HSV-1(F) viral genome is not expressed. The ICP35 encoded by the plasmid construct is expressed inasmuch as the transfected gene is regulated as a β gene.

In the preceding sections it was shown that the sequences encoding ICP35 overlapped only a portion of the sequence designated the UL26 ORF. The purpose of the studies presented in the following sections was to identify the product of the full length $U_L26$ open reading frame. BHK cells were transfected with plasmid construct O,N, or P(FIG. 1A). and then infected with HSV-2. The electrophoretically separated proteins from cells transfected with plasmids O,N, and P, were reacted with monoclonal antibodies to either HSV-1(H725) or CMV(CH28-2)(FIG. 7 lanes 4 through 6 and 8 through 10) and then autoradiographed to provide molecular weight markers (lanes 1 through 3). The salient features of the results were as follows:

(1) the plasmid constructs O and P containing the CMV epitope inserted in frame with UL26 specified proteins which formed two bands with electrophoretic mobilities corresponding approximately to proteins with apparent molecular weights of 75,000 to 78,000 (FIG. 7, lanes 4 and 6). The CMV monoclonal antibody did not react with ICP35 bands produced by plasmids O and P(lanes 4 and 6). The CMV epitope was inserted at the HpaI restriction endonuclease site(+832), i.e. before the translation initiation site of ICP35 at position +1099.

(2) All plasmid constructs made ICP35 which reacted with H725 monoclonal antibody against HSV-1 ICP35. The disparity in the electrophoretic mobilities of the ICP35 proteins made by plasmid constructs N and P reflect the insertion into plasmid construct N of the oligonucleotide encoding an additional 21 amino acids.

(3) The abundance of proteins specified by the entire $U_L26$ ORF relative to that of the ICP35 protein may be deduced from the observation that while both of the Mr75,000–78,000 kd proteins and the ICP35 react with the same monoclonal antibody, CH28-2, the reactivity or amount of the larger protein is considerably lower than that observed for ICP35.

The compelling evidence that the two proteins share amino acid sequences is based on the observation that construct J under conditions of overproduction of the $U_L26$ proteins yielded proteins which co-migrated with both the larger protein and ICP35 and reacted with the CH28-2 monoclonal antibody(arrow,FIG. 7, lane 7).

EXAMPLE 8
Characterization of $U_L26$ and $U_L26.5$ Proteins

Figure 8:
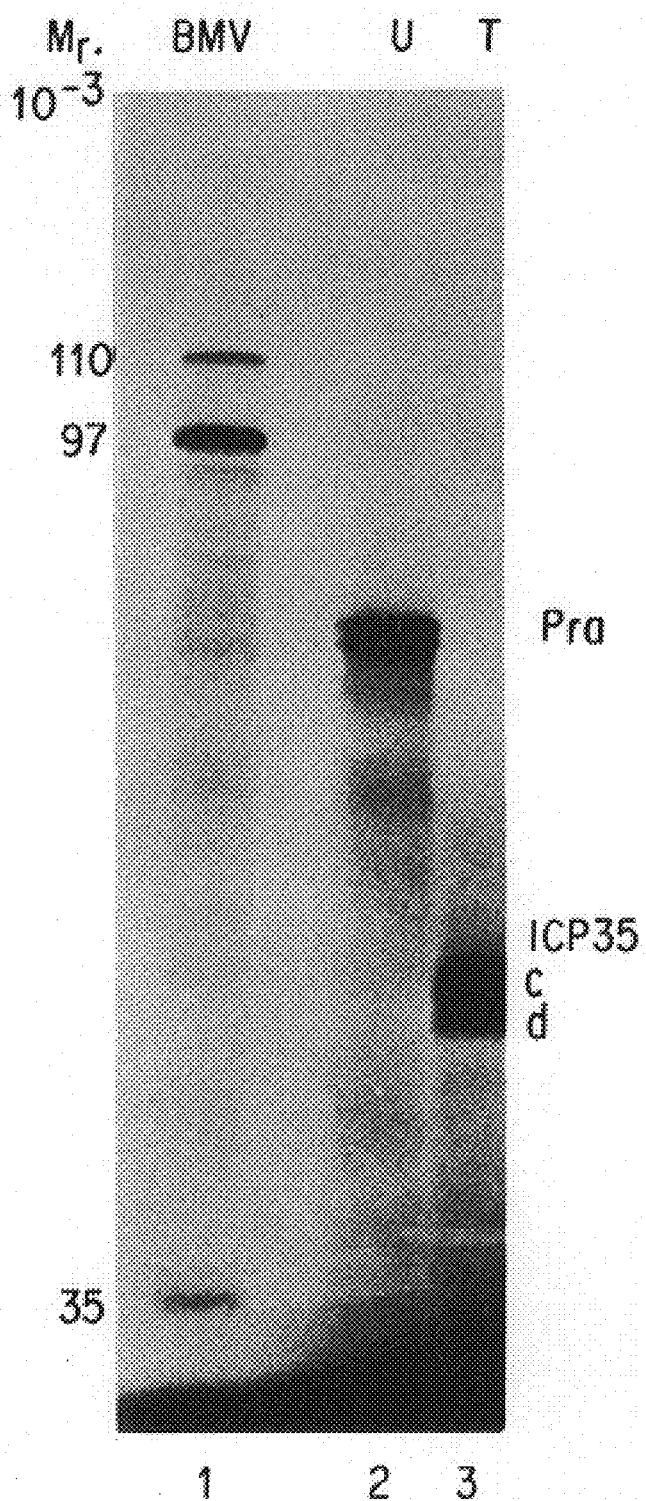
FIG. 8. Autoradiographic image of the $^{35}$S-methionine labeled polypeptides translated in a nuclease-treated rabbit reticulocyte lysate and electrophoretically separated in a 9.5% denaturing polyacrylamide gel.

An autoradiographic image of the $^{35}$S-methionine labeled polypeptides translated in a nuclease-treated rabbit reticulocyte lysate and electrophoretically separated in a 9.5% denaturing polyacrylamide gel are shown in FIG. 8.

In lane 1 are translation products of brome mosaic virus templates provided with a kit obtained form Promega Biotec, Wis. as transcribed according to the manufacturer's suggestions. Lane 2 shows translation products of the $U_L26$ open reading frame in plasmid U. Lane 3 shows the translation product of the $U_L26.5$ open reading frame in plasmid T. These results indicated that $U_L26$ and $U_L26.5$ specify proteins each of which form double bonds with apparent molecular weights of 80,000 kd (Pra) and 45,000 (ICP35d,c) respectively.

Figure 9:
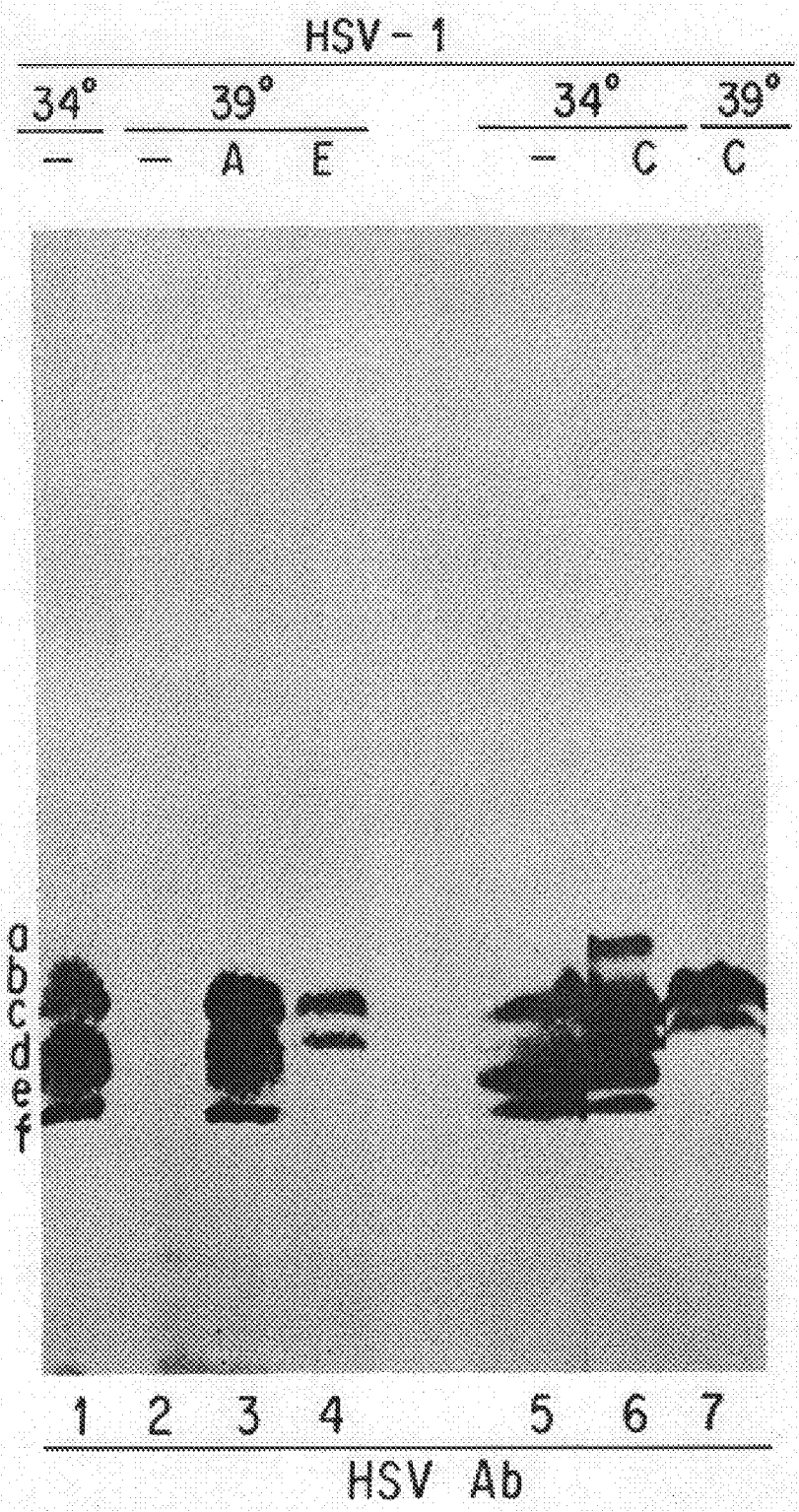
FIG. 9. Photograph of electrophoretically separated polypeptides from cells transfected with plasmid constructs and superinfected with HSV-1(F) either at 34° C. (34°) or at 39° C. (39°), electrophoretically separated in polyacrylamide gels, electrically transferred to a nitrocellulose sheet and reacted with monoclonal antibody H725 to HSV-1 ICP35 (HSV Ab) and stained with goat anti-mouse IgG antibody coupled to peroxidase.

EXAMPLE 9
The Gene Product of $U_L26$ is Required to Process ICP35c,d into e,f in Transposition A photograph of electrophoretically separated polypeptides from BHK cells transfected with plasmid constructs and superinfected with HSV-1(F) either at 34° C. (34°) or at 39° C. (39°), electrophoretically separated in polyacrylamide gels, electrically transferred to a nitrocellulose sheet and reacted with monoclonal antibody H725 to HSV-1 ICP35 (HSV Ab) and stained with goat anti-mouse IgG antibody coupled to peroxidase, is presented in FIG. 9. Experimental details are described in the Materials and Methods herein. The letters across the top of the gel identify the plasmid constructs with which the cells were transfected. A dash indicates that the cells were infected but not transfected. The letters on the side were assigned to different species of ICP according to Braun et al. (1984).

Figure 10:
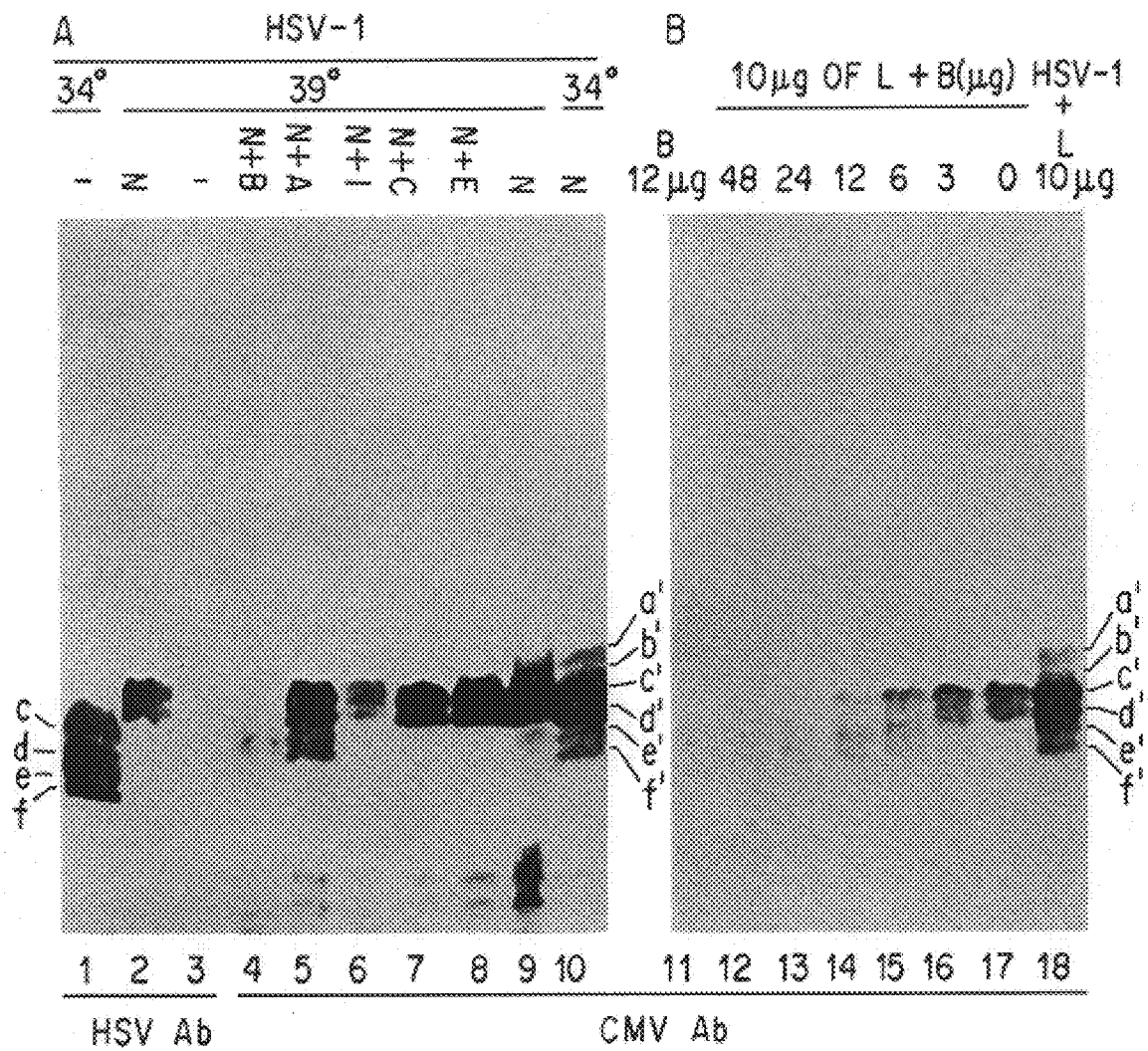
FIG. 10. Photograph of electrophoretically separated polypeptides from cells transfected with plasmids and either mock-infected or superinfected with HSV-1(F) (HSV-1) either at 34° C., at 39° C., or at 37° C., electrophoretically separated in polyacrylamide gels, electrically transferred to a nitrocellulose sheet, reacted with monoclonal antibody H725 (HSV Ab) or CH28-2 (CMV Ab) and stained with goat anti-mouse IgG antibody coupled to peroxidase.

Earlier experiments suggested that ICP35c, d were the precursors of ICP35e, f (Braun et al., 1984; Preston et al., 1983). To test this hypothesis, BHK cells were transfected with plasmid E containing $U_L26.5$ gene (FIG. 1A) and superinfected with HSV-1(F) at 39° C. This virus is temperature sensitive and at 39° C. it does not express its own $U_L26$ and $U_L26.5$ open reading frames. The results (FIG. 10) show the following:

(i) The ICP35 gene resident in the viral genome was expressed at 34° C. (lane 1) but not at 39° C. (lane 2) as evidenced by the presence and absence of the ICP35 bands reactive with the H725 monoclonal antibody to ICP35, respectively.

(ii) ICP35c, d were the only two species of ICP35 proteins expressed from the one reading frame in plasmid E at 39° C. (lane 4), whereas at least ICP35c, d, e and f could be detected in lysates of productively infected cells maintained at 34° C. (lane 1).

These results led to the conclusion that (i) ICP35c, d are the unprocessed forms of the ICP35 proteins, that (ii), they can be processed into ICP35e, f; and that (iii), the processing requires a transacting factor since processing did not occur in the absence of HSV-1(F) late gene expression.

EXAMPLE 10
The Protease Effects Carboxyl Terminal Cleavage

A photograph of polypeptides from cells transfected with plasmids and either mock-infected or superinfected with HSV-1(F) (HSV-1) or HSV-2(G) (HSV-2) either at 34° C. (34°, lanes 1 and 4), at 39° C. (39°, lanes 2 and 5), or at 37° C. (lanes 3 and 6–14), electrophoretically separated in denaturing polyacrylamide gels, electrically transferred to a nitrocellulose sheet, reacted with monoclonal antibody H725 (HSV-Ab) or CH28-2 (CMV Ab) and stained with goat anti-mouse IgG antibody coupled with peroxidase, is presented in FIG. 11. The letters across the top of the gel identify the plasmid constructs with which the cells were transfected. A dash indicates that the cells were infected but not transfected.

Another aspect of this invention is the type of cleavage effected by the protease. Processing of ICP35c, d to e, f involves carboxyl terminal proteolytic cleavage.

Inasmuch as ICP35e, f specified by plasmid N comigrated in denaturing gels with ICP35c, d produced in HSV-1 infected cells (FIG. 11, Panel 1, lanes 1 and 5), it may be deduced that the portion of the ICP35 cleaved during processing is roughly equivalent to the size of the CMV amino acid sequence inserted into plasmid N. To determine whether ICP35 processing involves carboxyl terminal proteolytic cleavage, BHK cells were transfected with plasmids J, R, S and W and superinfected with HSV-2. Plasmid R contained the CMV epitope (sequence A) inserted in the PmlI site of $U_L26.5$ whereas in plasmids S and W the insert was at the carboxyl terminal amino acid. Analyses of the electrophoretic separated, electrically transferred polypeptides with the anti HSV-1 (H725) and anti CMV (CH28-3) monoclonal antibodies revealed the following (FIG. 12):

(i) Cells transfected with plasmid J in which the CMV epitope was inserted at the MstII site 122 amino acids upstream from the $U_L26$ stop codon made both the precursor ICP35c, d and products ICP35 e, f which reacted with the CMV antibody (lane 8). The decrease in the electrophoretic mobility of ICP35c, d, e and f relative to the wild type proteins corresponds to the increase in the molecular weight due to the insertion of the CMV epitope.

Figure 11:
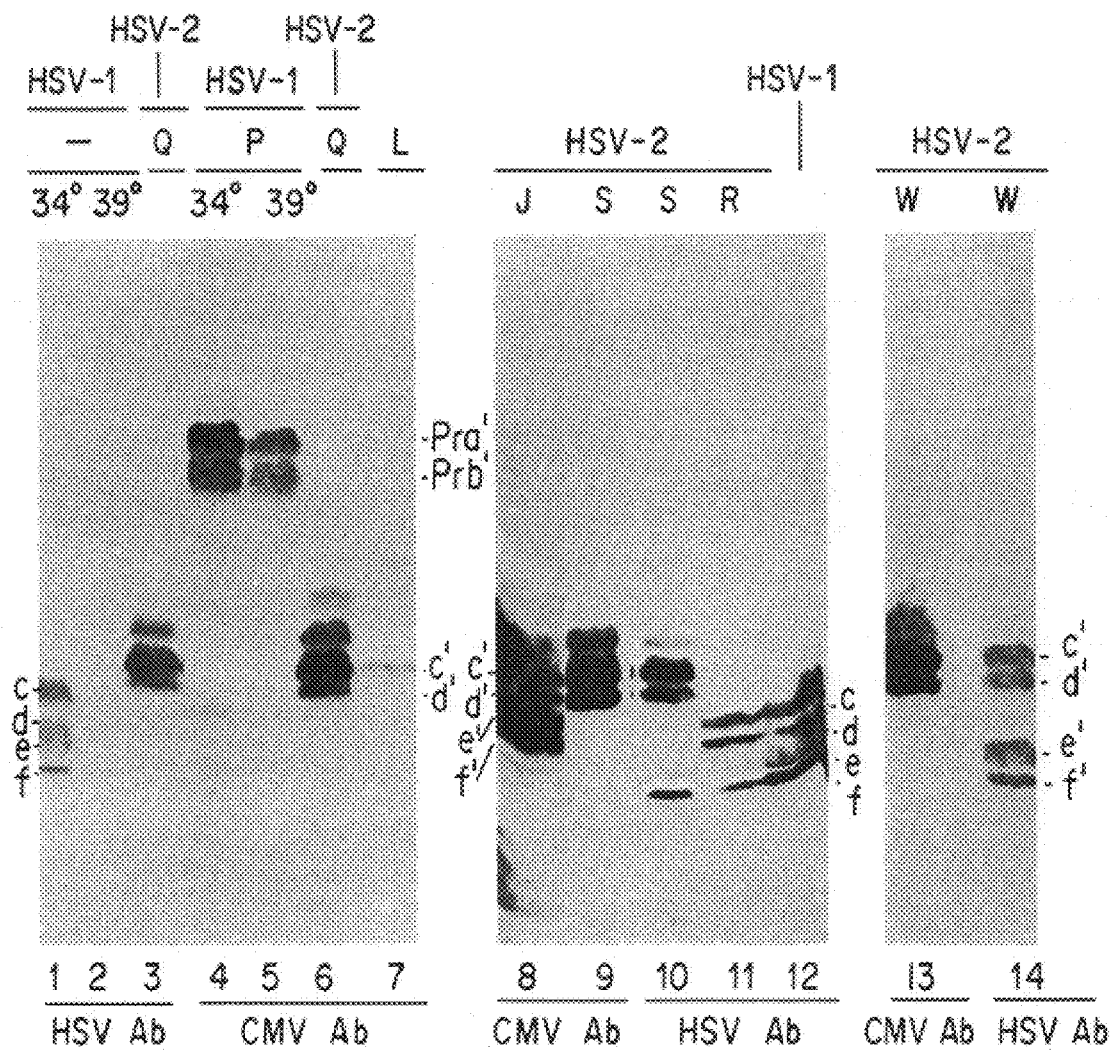
FIG. 11. Photograph of polypeptides from cells transfected with plasmids and either mock-infected or superinfected with HSV-1(F) (HSV-1) or HSV-2(G) (HSV-2) either at 34° C., at 39° C., or at 37° C., electrophoretically separated in denaturing polyacrylamide gels, electrically transferred to a nitrocellulose sheet, reacted with monoclonal antibody H725 (HSV-Ab) or CH28-2 (CMV Ab) and stained with goat anti-mouse IgG antibody coupled with peroxidase.

(ii) Only ICP35c, d were made in cells transfected with plasmid Q (Lanes 3 and 6). In this plasmid the CMV epitope was inserted into the PmlI site of $U_L26$, which is 21 amino acids upstream from $U_L26.5$ stop codon. The identification of the ICP35c, d forms was based on the observation that they co-migrated with the corresponding forms specified by plasmid L which expressed only ICP35c, d in transfected cells (FIG. 11, Panel B, lane 17).

(iii) Insertion of sequence C into plasmid R at PmlI restriction endonuclease site destroyed this site and created a new PmlI cleavage site between the carboxyl terminal amino acid and the stop codon of $U_L26$ without changing the amino acid sequences of either $U_L26$ or $U_L26.5$. ICP35c, d, e and f detected with H725 monoclonal antibody co-migrated with the authentic proteins (lane 11), indicating the insertion of sequence C had no effect on ICP35 expression and processing.

Figure 12:
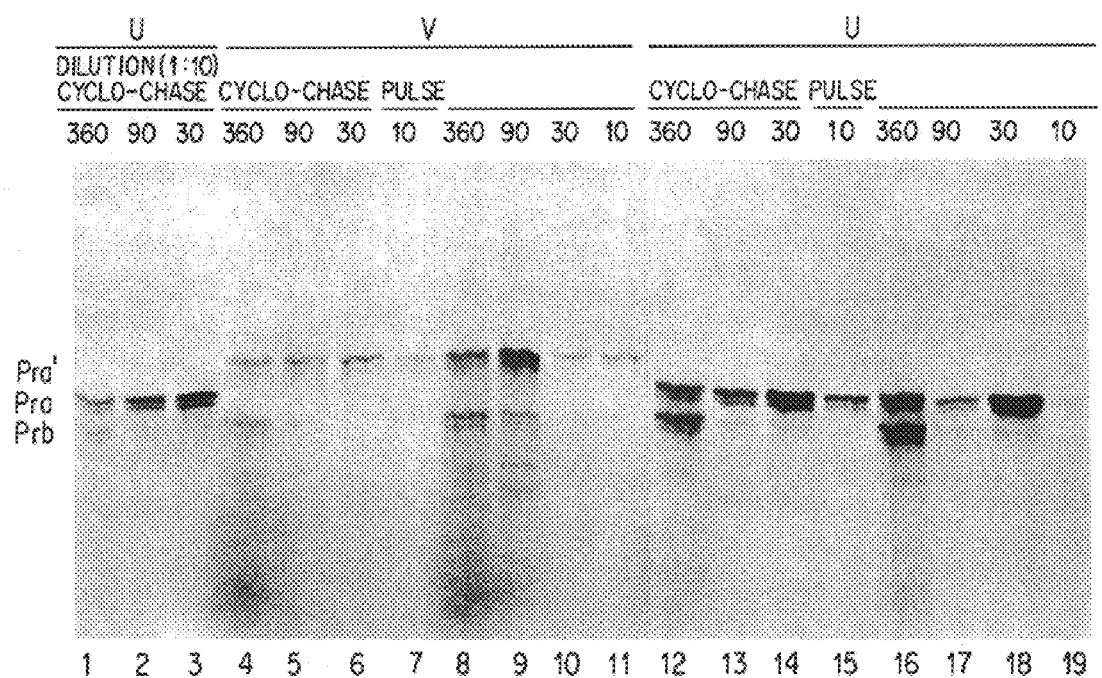
FIG. 12. Autoradiographic image of $^{35}$S-methionine labeled polypeptides encoded by the $U_L26$ open reading frame electrophoretically separated in a denaturing polyacrylamide gel.

(iv) In plasmid S and W the CMV epitope was inserted into the new PmlI site of plasmid R at the carboxyl terminus of $U_L26.5$. Cells transfected with these plasmids accumulated ICP35c, d e, and f reactive with HSV-1 H725 monoclonal antibody (lanes 10, 14) but only the ICP35c and d forms reacted with the CMV CH28-2 monoclonal antibody (lanes 9, 14). The significant finding is that whereas ICP35c, and d forms of plasmid S co-migrated with the corresponding forms of plasmid J, i.e. they were 21 amino acids longer than wild type, the ICP 35e, f indicating that the inserted amino acid sequence encoding the CMV epitope was removed (lanes 9 and 10). The products specified by plasmid W behaved in the same manner (FIG. 12). ICP35e, and f specified by plasmid W were more abundant than those specified by plasmids S and R possibly because in plasmid W the entire $U_L26$ open reading frame was reconstituted and more of the protein product was expressed and made available to process ICP35.

The cleavage of the precursor ICP35 protein is approximately 20 amino acids from the carboxyl terminal codon. Evidence for this conclusion was that (i) insertion of the CMV epitope 21 amino acids from the terminus interfered with the cleavage, whereas insertion of the epitope at the carboxyl terminus enabled the cleavage to take effect; (ii) the comigration of ICP35e', and f' (with CMV epitope) and ICP35c, d. The comigration places the CMV-insertide e and f in the same approximate gel location as c, d in the authentic protease.

An unexpected correlation between the cleavage mechanism used to produce the ICP35 subunits and to autoprocess the $U_L26$ protease was that both involve carboxyl terminal proteolytic cleavage. In the preceding sections, it was demonstrated that $U_L26$ is the only viral factor responsible for the carboxyl terminal proteolytic processing of ICP35. $U_L26$ coding for the protease and $U_L26.5$ coding for ICP35 also share the same carboxyl terminal amino acid sequence. The possibility that $U_L26$ cleaves itself emerged from the observation that in BHK cells transfected with plasmid P (FIG. 1A) and superinfected with HSV-1(F) either at 34° C. or at 39° C. expressed a doublet band of $U_L26$ (FIG. 5, lane 4 and 5) which reacted with CH28-2 monoclonal antibody. This observation suggested the possibility that $U_L26$ may catalyze its own cleavage because HSV-1(F) expresses primarily to α genes at 39° C.

EXAMPLE 11
The Protease Cleaves Itself

In FIG. 12 an autoradiographic image of $^{35}$S-methionine labeled polypeptides encoded by $U_L26$ open reading frame, and electrophoretically separated in a denaturing polyacrylamide gel, is shown. The $U_L26$ open reading frame contained in plasmids U and V (FIG. 1A) was transcribed in vitro and translated in a nuclease-treated rabbit reticulocyte lysate. The lanes shown represent positions removed from the translation mixture at 10, 20, 90, and 360 minutes post initiation of translation. For samples shown in lanes 4–7 and 12–15, cycloheximide was added to the translation mixture at 10 minutes post initiation of translation to inhibit further translation. In the case of lanes 1–3, the translation mixture at 10 minutes post initiation of translation was diluted 10-fold in phosphate-buffered saline containing cycloheximide (100 μg/ml).

Additional evidence that $U_L26$ can catalyze its own cleavage emerged from in vitro studies. RNA transcribed from plasmids U or V (FIG. 1A) in vitro by T7 of Sp6 RNA polymerases were translated in a nuclease treated rabbit reticulocyte lysate in the presence of [$^{35}$S]-methionine. Analyses of the electrophoretically separated products of the translation reaction were as follows (FIG. 12):

(i) Incubation of the translation products of the U plasmid in the presence of cycloheximide resulted in gradual accumulation of the cleavage product (Prb) of the $U_L26$ protein. The amount of accumulated cleavage product was proportional to the duration of the incubation (lanes 16–19).

(ii) Identical results were obtained with the translation of products of plasmid V. The significance of this experiment stems from the presence of the CMV epitope at the carboxyl terminus of $U_L26$. As expected, the precursor form of $U_L26$ made from plasmid V migrated more slowly than the authentic protein derived from plasmid U. However, the processed from of $U_L26$ synthesized from plasmid V co-migrated with that of the authentic protein from plasmid U, indicating that the $U_L26$ autoprocessing involves carboxyl terminal proteolytic cleavage.

Figure 13:
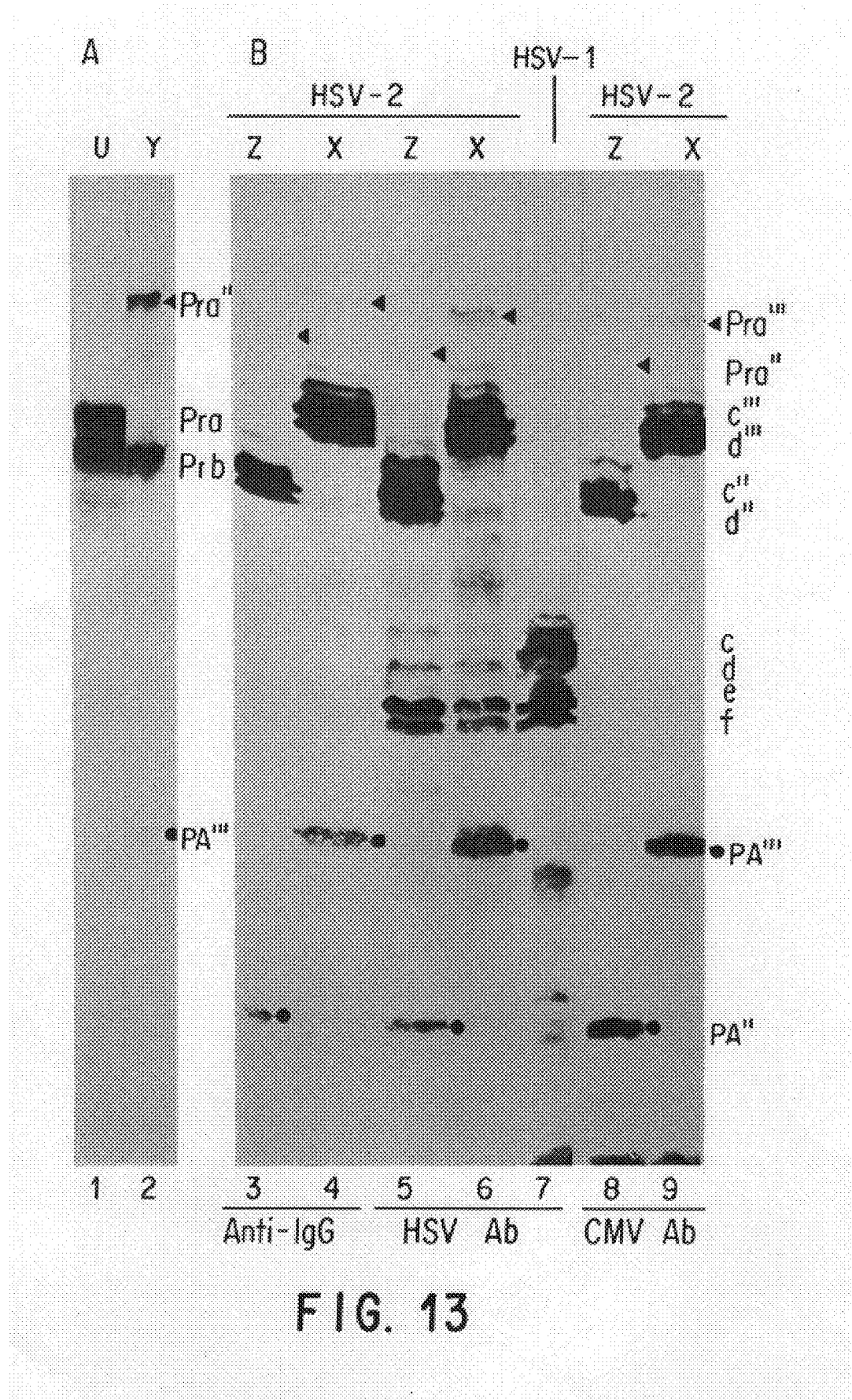
FIG. 13. Autoradiographic images and photograph of polypeptides either synthesized in vitro from sequences encoded in plasmids U or Y or contained in lysates of cells transfected with plasmids X or Z and superinfected with HSV-1(F) or HSV-1(G).

EXAMPLE 12
Cleavage of ICP35c,d and Pra are Sequence Specific and are at the Same Site Autoradiographic images (Panel A) and a photograph of polypeptides (Panel B) either synthesized in vitro from sequences encoded in plasmids U or Y or contained in lysates of cells transfected with plasmids X or Z and superinfected with HSV-1(F) or HSV-1(G) are presented in FIG. 13. The in vitro synthesized polypeptides and those contained in cells lysates were electrophoretically separated in the same denaturing 12% polyacrylamide gel, electrically transferred to a nitrocellulose sheet, and reacted with monoclonal antibody anti-mouse IgG conjugated with horseradish peroxidase (Anti-IgG) only, or with this anti-IgG antibody in addition to the monoclonal antibody H725 (HSV Ab) or CH28-2 (CMV Ab). A dash indicates that the cells were infected but not transfected. The polypeptides shown in panel A were labeled with $^{35}$S-methionine. The band designations were as follows: letters c, d, e, f, without primes identify authentic ICP35 products of $U_L26.5$ open reading frame. Pra and Prb are the translation processed forms of the protease products of the $U_L26$ open reading frame. The double and triple primes indicate that the protein also contains the CMV epitope and the sequence encoding two IgG and five IgG binding domains of staphylococcus protein A, respectively. PA'' and PA''' are the carboxyl terminus products of the cleavage of the ICP35c, d and Pra proteins containing inserts of CMV epitope and IgG binding domains.

The cleavage of ICP35c, d and Pra are sequence-specific and are at the same site. The results of the experiments presented herein suggested that the cleavage/processing of the products of $U_L26$ and $U_L26.5$ occurred at a site approximately 18–25 amino acids from the carboxyl terminus of the proteins. To demonstrate that the processing of these proteins occurs at the predicted site, it was necessary to demonstrate both products of the cleavage reaction on the same gel. In order to visualize both products, it was necessary to insert into the coding sequence at the predicted carboxyl terminus both the epitope for the CMV monoclonal antibody and the sequences encoding the IgG binding domains of staphylococcal protein A. Plasmids X and Z were constructed by inserting in frame the sequences coding for 129 and 256 amino acids comprising two and five IgG binding domains of protein A, respectively, in frame between the 3' terminus of the CMV epitope and the stop codon of $U_L26$ (FIG. 1).

Two experiments were done. In the first, the HSV-1 open reading frames in plasmids U and Y were transcribed and translated for six hours. The proteins translated in vitro were then electrophoretically separated in a denaturing gel (FIG. 8, Panel A). In the second experiment, BHK cells were transfected with plasmids Z or X and then superinfected with HSV-2(G). The cell lysates were electrophoretically separated in the same gel as that used for the separation of the in vitro translated protein, electrically transferred to a nitrocellulose sheet, and reacted with antibody to CMV, HSV, or with anti-IgG antibody that would bind to IgG binding domains of protein A (FIG. 8, Panel B). The results were as follows:

(i) Autocatalytic processing of the in vitro transcribed, translated HSV-1 sequences in plasmid U yielded as expected the protein bands designated as Pra and Prb. Similar autocatalytic processing of the products of the Z band yielded three bands. The first band migrated slower than the authentic precursor Pra band, as would be expected from the presence of additional 256 amino acids of protein A and the 21 amino acids constitution the CMV epitope. The second band co-migrated with the Prb band and is therefore the product of the autocatalytic cleavage of the translation product. The third band co-migrated with the bands described below and which reacted with the CMV as well as with the anti-IgG antibody.

(ii) the expected translation products of the plasmid X were ICP35c, d and Pra. It could be expected that the translation products of the plasmid Z should be similar except that, because of the smaller inserts of the protein A sequences, these proteins should migrate correspondingly faster than those of the plasmid X. This was in fact the case (compare lanes 3,5 and 8 with those of 4, 6 and 9). It could also be predicted that if the cleavage of the ICP35c, d, occurs as expected 20 amino acids from the carboxyl terminus of the authentic protein, that the amino terminus products of the cleavage reaction should co-migrate with the authentic ICP35 and react only with the HSV-1 monoclonal antibody. This was in fact the case inasmuch as ICP35e and f produced by plasmid Z and X (lanes 5 and 6) co-migrate with the authentic ICP35e and f (lane 7) and were detectable solely by the HSV-1 specific monoclonal antibody. Conversely, it could be expected that the carboxyl terminus products of the cleavage reaction should migrate in accordance with their size, and should react with both anti IgG and CMV antibodies. As shown in Panel B of FIG. 7 the bands reactive with the anti IgG antibody from lysates of cell transfected with plasmid X migrated slower than the corresponding Z bands. However, because all of the carboxyl terminal cleavage products contained the IgG binding domains of protein A, all of the protein products would be expected to react with IgG irrespective of specificity of the immunoglobulin (e.g., bands 5 and 6).

Inasmuch as both products were detected, the results indicate that ICP35c, d and Pra the products of the $U_L26.5$ and $U_L26$, respectively, are both translationally processed by cleavage. Because the two proteins share amino acid sequences for the entire length of ICP35c, d and because the products of the cleavage of the two proteins co-migrate, the two proteins are cleaved at identical sites. Finally, the translational products of both open reading frames in vitro resolve into double bands. The double bands are particularly noticeable in the case of ICP35 (forms c and d). In all of the experiments done to date including those shown in FIG. 8 the carboxyl terminal product of the cleavage formed a single band. This observation is consistent with the hypothesis that the differences in the proteins which form the doublets are at the amino rather than the carboxyl termini of the proteins.

Figure 14:
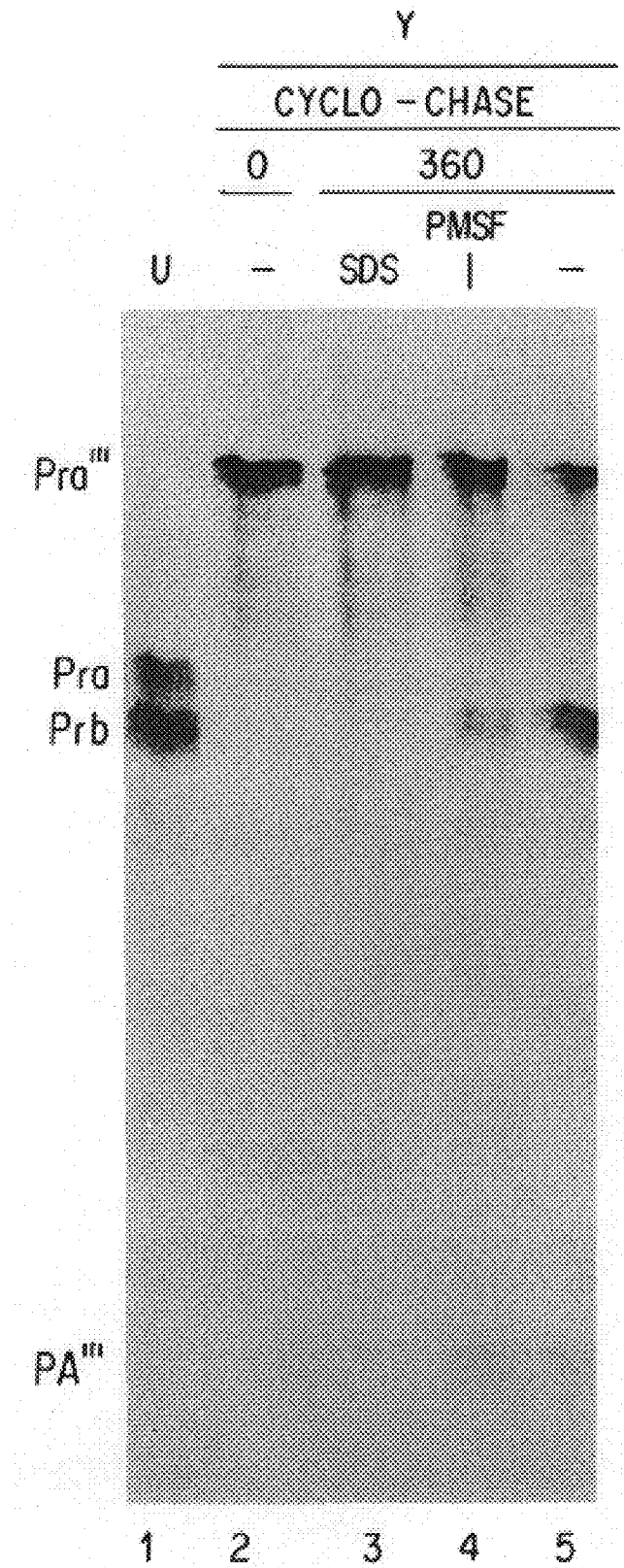
FIG. 14. Autoradiographic image of $^{35}$S-methionine labeled polypeptides encoded by the $U_L26$ open reading frame electrophoretically separated in a denaturing gel to show the action of PMSF as a protease inhibitor.

As shown in FIG. 14, the autoradiographic image of $^{35}$S-methionine labeled polypeptides encoded by $U_L26$ open reading frame electrophoretically separated in a denaturing gel. The $U_L26$ open reading frame contained in plasmid U and Y (FIG. 1A) was transcribed in vitro and translated in nuclease treated rabbit reticulocyte lysates. Lane 1 shown represents the portion removed from the translation mixture at 360 minutes post initiation of translation. Lanes 2–5 shown represent portions removed from the translation mixture either at 10 minutes (0) or at 360 minutes (360) post initiation of translation. For samples shown in lanes 2–5, the equivalent amount of translation mixture at 10 minutes post initiation of translation was diluted 20-fold in phosphate-buffered saline containing cycloheximide (100 microgram/ml) and either sodium dodecyl sulphate (SDS) (0.4%) (lane 3) or phenylmethanesulfonyl fluoride (PMSF) (500 microgram/ml (lane 4).

EXAMPLE 13
Detection of a Candidate Inhibitor Substance

In still further embodiments, the present invention concerns a method for identifying new herpes viral protease inhibitory compounds, which may be termed as "candidate substances." It is contemplated that this screening technique will prove useful in the general identification of any compounds that will serve the purpose of inhibiting the herpes protease. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the enzyme, and serve to inactive the enzyme through a tight binding or other chemical interaction.

Thus, in these embodiments, the present invention is directed to a method for determining the ability of a candidate substance to inhibit a herpes protease, the method including generally the steps of:

(a) obtaining a composition comprising a herpes protease that is capable of cleaving its own amino acid sequence, or cleaving the ICP35 protein or any amino acid sequence containing the cleavage site for this protease;

(b) admixing a candidate substance with the protease composition; and (c) determining the ability of the protease to effect cleavage in the presence of the candidate substance.

An important aspect of the candidate substance screening assay hereof is the ability to prepare a protease composition in a relative purified form, for example, in a manner as discussed above. This is an important aspect of the candidate substance screening assay in that without at least a relatively purified preparation, one will not be able to assay specifically for protease inhibition, as opposed to the effects of the inhibition upon other substances in the extract which then might affect the protease. In any event, the successful isolation of the protease now allows for the first time the ability to identify new compounds which can be used for inhibiting this herpes related protein.

The candidate screening assay is quite simple to set up and perform, and is related in many ways to the assay discussed above for determining protease activity. This, after obtaining a relatively purified preparation of the protease, one will desire to simply admix a candidate substance with the protease preparation, preferably under conditions which would allow the protease to perform its cleavage function but for inclusion of a inhibitory substance. Thus, for example, one will typically desire to include within the admixture an amount of a known protease substrate such as the amino acid sequence coded by the $U_L26.5$ coding sequence or at least the cleavage site at which the protease cleaves ICP35 c, d into e and f. In this fashion, one can measure the ability of the candidate substance to reduce or alter cleavage of the herpes protease substrate relatively in the presence of the candidate substance.

Accordingly, one will desire to measure or otherwise determine the activity of the relatively purified protease in the absence of the assayed candidate substance relative to the activity in the presence of the candidate substance in order to assess the relative inhibitory capability of the candidate substance.

In still further embodiments, the present invention is concerned with a method of inhibiting a protease which includes subjecting the protease to an effective concentration of a protease inhibitor such as one of the family of peptidyl compounds discussed above, or with a candidate substance identified in accordance with the candidate screening assay embodiments. This is, of course, an important aspect of the invention in that it is believed that by inhibiting the herpes protease, one will be enabled to treat various aspects of herpes infections. It is believed that the use of such inhibitors to block the action of the protease to produce capsid proteins will serve to treat or palliate the infection, and may be useful by themselves or in conjunction with other herpes therapies.

As shown in FIG. 14, PMSF was capable of partially inhibiting the protease self-cleavage. In lane 5, normal self cleavage is shown. In line 3, 100% inhibition by SDS.

SUMMARY OF GENERAL METHODS

1. Markers (Tracers)

Two monoclonal antibodies were used as markers (tracers), one to a stationary epitope encoded by both $U_L26$ and $U_L26.5$ open reading frames and one reactive with a "movable epitope." The latter was an indispensable tool in the identification of the products of the two open reading frames, in the determination of the function of the proteins, and in mapping of the cleavage site. Without the "movable epitope," analysis would depend solely on radioactive tracers or monoclonal antibodies to oligopeptides corresponding to various domains of the genes. The movable epitope offers instant antibody to the product of any open reading frame and, when used in the context of the present invention, it enormously facilitated identification of the function of the product of the gene into which it has been inserted.

By inserting the coding sequence of an epitope reactive with a cytolomegalovirus monoclonal antibody and homologs of the IgG binding domain of staphylococcus protein A into the 3' termini of the coding domains of the two open reading frames, the products of the protease cleavage were identified, the cleaved protease, designated Prb, and ICP e and f. It was also determined by this methodology that the cleavage site for the ICP35 proteins and that separating the total protease sequence into Pra and Prb, is approximately 20 amino acids from the carboxyl termini of both the protease and the ICP precursor.

As an example of the investigation of the herpes genome using plasmids with markers, the effect of one of the marker-inserted plasmids, S (FIG. 1A), used to transfect cells with a portion of the herpes genome is illustrative. In this plasmid the CMV epitope was inserted at the carboxyl terminus of the sequence of ICP35. The cells infected with a portion of the herpes genome in this fashion were then collected and disrupted so that proteins within the cells could be analyzed. These proteins were then electrophoretically separated by molecular weight into bands. ICP35 is immunologically identifiable by the HSV antibody. The CMV epitope was sought among the bands by applying the antibody to the epitope and detecting a signal indicating the production of an antigen-antibody complex. Results of this immunological analysis showed that the CMV epitope was detected in bands c and d, but not in e and f. This indicated that cleavage of the carboxyl terminus of c and d had taken place to form e and f.

2. Cell Free Protein Synthesis

Another useful technique was a cell free protein synthesizing system. RNA's corresponding to the mRNA'S of $U_L26$ and $U_L26.5$ were transcribed by Sp6 RNA polymerase and translated in nuclease-treated rabbit reticulocyte lysates, a cell-free, "ribosome machine." The proteins translated in cell free systems in vitro were labelled with radioactive labels, separated by gel electrophoresis, and subjected to autoradiography to locate the band containing labels. There were two sets of experiments using this general methodology:

(i) Incubation of the translation products of the U plasmid in the presence of cycloheximide which resulted in gradual accumulation of the cleavage product (Prb) of the $U_L26$ protein. The amount of accumulated cleavage product was proportional to the duration of the incubation (FIG. 12, lanes 12–15).

(ii) Identical results were obtained with the translation products of plasmid V (lanes 4–7). The significance of this experiment stems from the presence of the CMV epitope at the carboxyl terminus of $U_L26$. As expected, the translation product Pra of $U_L26$ made from plasmid V migrated more slowly than the authentic protein derived from plasmid U. However, the processed form Prb of $U_L26$ synthesized from plasmid V comigrated with that of the authentic protein from plasmid U, indicating that the $U_L26$ autoprocessing involves carboxyl terminal proteolytic cleavage.

3. HSV-1(F), a Temperature Sensitive Mutant

Another tool used in the analysis of the HSV genome was HSV-1(F), a temperature sensitive mutant which at 39° C. does not express its own $U_L26$ and $U_L26.5$ open reading frame. Rather, HSV-1(F) at the non-permissive temperature induces α-gene promoters (Post et al., 1981) and expresses primarily the a type genes.

4. Identification and Use of Protease Inhibition

If the action of the protease is inhibited, the capsid cannot be produced and the virus will not be replicated. This inhibition may be either at the level of transcription, translation, or protein action. Interference with transcription would necessitate interference with mRNA formation on a DNA template. Interference with translation would necessitate interfering with the synthesis of proteins on the mRNA template. Alternatively, the action of the protease may itself be disrupted either by destroying the structure of the protease, in particular its proteolytic module, altering the cleavage site of its substrate, or binding the protease to irreversible inhibitors.

Specifically designed peptides which block the function of the protease are extremely valuable in preventing and treating herpes infections. Embodiments of these blockers include any substrate analogues or serine protease inhibitor, e.g., oligopeptides or their derivatives which contain the amino acid sequence of the cleavage site recognized by the protease. Methods for identifying suitable protease inhibitors from candidate substances are disclosed in Example 13.

It is an additional object of the present invention to provide a ready means for producing the viral protease for use in detecting inhibitors, to develop treatment modalities, to develop antibodies for detection of viral infection, and to develop inactive mutants of the protease.

An exemplary embodiment for preparing the protease protein is to prepare a nucleic acid segment which includes a nucleic acid sequence capable of encoding the desired protease protein or polypeptide. This segment may be that which encodes the entire protease or only some portion of it, for example, the proteolytic domain of the protease. The segment may be as small as that capable of triggering a positive signal with an antibody, thereby, identifying the presence of a viral infection. Segments functionally equivalent to those shown in FIG. 1A, which were developed in the present invention, may also be selected depending on the desired polypeptide to be produced. Functional equivalence may be determined by testing whether the segment can cleave either the ICP35 precursor or the Pr protease, for example, using techniques disclosed herein to detect protease inhibitors from among candidate substances.

The nucleic acid segment selected is transferred into an environment appropriate for expression of the segment as a polypeptide. This environment may be a vessel containing a mixture capable of inducing expression, e.g., a rabbit reticulocyte lysate. Alternatively, the segment may be transferred to a host cell by transformation, transfection via a recombinant expression vector, electroporation, or a "gene gun." The host cell may be selected from BHK cells, Vero, Hela, E. coli, and the like.

The recombinant expression vector may include a promoter. Embodiments of promoters are the α4 promoter, the native promoter of $U_L26.5$, and any other prokaryotic or eukarystic promoters.

In another embodiment, the nucleic acid segment may be prepared by obtaining genomic nucleic acids from herpes cells, amplifying a proteolytic site-conserved nucleic acid sequence region within the genomic nucleic acids, preparing recombinant clones which include said amplifying nucleic acid sequences, and selecting clones which comprise the desired amplified nucleic acid sequence.

The viral protease may also be prepared by obtaining a sample which contains the protease, homogenizing the sample, and fractionating the homogenate to obtain a protease fraction. Samples which contain the protease will include biological samples, for instance, virally infected tissues.

5. Treatment of Herpes Infections

Treatment modalities contemplated include topical and systemic medicants. For dermal and epidermal lesions, creams, ointments or sprays containing a protease inhibitor, are contemplated. Alternatively, systemic treatment by intravenous injection or ingestion is envisioned to prevent the deleterious outbreak of viral replication due to reactivation of latent viral inhabitants of host cells.

6. Virus and Cells

The properties of HSV-1(F) and HSV-2(G), the prototype HSV-1 and HSV-2 strains, respectively, used in this invention, and the maintenance and propagation of the thymidine kinase minus baby hamster kidney (BHK) cells have been described previously and are incorporated herein by reference(Arsenakis et al., 1986; Ejercito et al., 1968; Roizman and Spear, 1968).

7. Monoclonal Antibodies

Monoclonal antibody H725 and CH28-2 to ICP35 and CMV glycoprotein B, respectively, have been described previously (Braun et al., 1983, 1984). Monoclonal antibodies used in these studies were obtained from Lenore Pereira. (see also Zweig, 1980) The monoclonal antibody H725 reacts with ICP35 of HSV-1 but not with HSV-2 proteins (Braun et al., 1983, 1984). CH28-2, a gift of L. Pereira, is a monoclonal antibody directed against human cytomegalovirus (CMV) glycoprotein A. The epitope of this antibody has been mapped to a 20-amino-acid peptide, N-KGQKPNLLDRLRHRKNGYRH-C, by assaying the reactivity of a series of overlapping peptide synthesized according to the predicted nucleotide sequence of the protein.

8. In Vitro Transcription and Translation

5 µg of Plasmid DNA templates were prepared and transcribed in the presence of capped analog GppG (New England Biolabs, Mass.) with Sp6 or T7 RNA polymerase as recommended by Promega Biotec, Madison Wis., 1 µg of either synthetic RNAs or BMV RNA supplied by Promega Biotec was translated in a 50 µl reaction mixture containing nuclease-treated rabbit reticulocyte lysate and [$^{35}$S]-methionine (DuPont, NEN, Mass.) by using a kit from Promega Biotec. After incubation of translation reaction mixture at 37° C. for different time intervals the translation reaction was either terminated by the addition of disruption buffer [0.05 M Tris, pH7.0; 85% (vol/vol) sucrose; 5% (vol/vol) 2-β-mercaptoethanol and 2% (vol/vol) sodium dodecyl sulfate (SDS)] or by the addition of cycloheximide (Sigma, St. Louis) to a final concentration of 100 µg/ml. In some experiments, the translation mixture was diluted 10 fold in phosphate-buffered saline containing cycloheximide with final concentration of 100 µg/ml. In all cases, the contents of the reaction mixtures were solubilized in disruption buffer and boiled for 1 minute before electrophoretic separation in denaturing gels.

9. Transfections and Superinfection of Cells Transfected With Plasmid DNAs

Transfections were done as described by Kristie and Roizman (1984) except that wells were generally transfected with 10 ug of plasmid DNA 6-well Costar (Cambridge, Mass.) dish cultures of BHK, cells contained approximately $10^6$ cells per well. In most experiments, the transfected cells were exposed 18 to 20 hours post transfection to 10 pfu of HSV-1(F) or HSV-2(G) per cell as stated in the Results. After 2 hours of exposure of cells to virus at 10° C., the inoculum was replaced with Dulbecco's modified Eagle's medium supplemented with 10% fetal bovine serum and the cells were incubated at 34° C., 37° C., or 39° C. for 20 hours. In the experiments which did not involve viral infection, the cells were harvested 40–42 hours post transfection. At 20 hr. postinfection, cells were labelled for 2 hr with 50 µCi of $^{35}$S methionine in 1 ml of medium (199 without methionine supplemented with 1% calf serum). The harvested cells were washed once with phosphate-buffered saline, pelleted by centrifugation at about 4,000 rpm for 5 min in a SS34 Sorvall rotor spun in a DuPont centrifuge, suspended in the disruption buffer, sonicated for 20 seconds in ice, and boiled for 1 minute before electrophoretic separation in denaturing gels.

10. Electrophoretic Separation and Staining of Infected Cell Proteins With Monoclonal Antibody The denatured, solubilized polypeptides from cell lysates or in vitro translation were separated on 9.5% or 12% (vol/vol) SDS-polyacrylamide gels crosslinked with N,N'-diallyltartardiamide as described by Gibson and Roizman (1972, 1974), and Braun et al. (1984). The separated polypeptides from BHK cells were transferred electrically to nitrocellulose membranes and reacted in an enzyme-linked immunoassay with only anti-mouse IgG conjugated with horseradish peroxidase (Amersham, Arlington Heights, Ill.) or with this anti-mouse IgG in addition to the monoclonal antibodies H725 against HSV-1, ICP35 or CH28-2 against CMV epitope, as previously described (Braun et al., 1984). The gels containing the separated polypeptides translated from the reticulocyte lysate were dried and exposed to Kodak X-Omat film.

11. Isolation and S1 Analysis of Cytoplasmic RNA

Cytoplasmic RNA was purified as described previously by Jenkins and Howett (1984) from Vero cells mock infected or infected with 20 PFU of HSV-1(F) per cell and maintained for 12 h. HSV-1 DNA probe (0.02 pmol) was 5' end labeled with [$\gamma^{32}$P]ATP (Dupont, NEN Research Products), hybridized to 50 µg of total cytoplasmic RNA, digested with S1 nuclease, and separated on 7% polyacrylamide gels in the presence of 8 M urea (Jenkins and Howett, 1984).

12. Methods of Preparing the Proteins of the Present Invention

Recombinant vectors are useful both as a means for preparing quantities of the protease or ICP35 encoding DNA itself, or as a means for preparing the encoded proteins. It is contemplated that where proteins of the invention are made from recombinant means, one may employ either prokaryotic or eukaryotic expression systems.

Where expression of herpes nucleic acid segments in a eukaryotic host is contemplated, it may be desirable to employ a vector, such as a plasmid, that incorporates a eukaryotic origin of replication, as exemplified by vectors of the pCMV series, like pCMV4. Additionally, for the purposes of expression in eukaryotic systems, one will desire to position the protease or ICP35 encoding sequence adjacent to and under control of an effective eukaryotic promoter, such as an SV40 or CMV promoter. To bring a coding sequence under the control of a promoter, whether it be a eukaryotic or prokaryotic promoter, all that is generally needed is to position the 5' end of the transcription initiation site of the transcriptional reading frame of the protein between about 1 and about 50 nucleotides downstream of the promoter chosen.

Furthermore, where eukaryotic expression is contemplated, one will desire to incorporate into the transcriptional unit which includes the desired peptide or protein, an appropriate polyadenylation site(e.g. 5'-AATAAA-3'). Typically, the poly A site is placed about 30 to 2000 nucleotides "downstream" of the termination site of the protein at a position prior to transcription termination.

Useful eukaryotic vectors which include all of the foregoing, and into which the herpes genes of the present invention can be inserted with little difficulty are well known. For example, suitable vectors include pCD and pCMV, with the most preferred system being pCMV. In addition to pCD and pCMV vectors, other preferred eukaryotic expression vectors include pMSG and pSVL from Pharmacia LKB Technology, Piscataway, N.J. These utilize the MMTV and SV40 late promoters, respectively. A cDNA incorporating the entire reading frames of the herpes protein, such as shown in FIG. 1., can be readily inserted into one of the foregoing vectors via the HindIII restriction site (AAGCTT) "upstream" of (i.e. 5' of) the initiation codon (ATG) that begins translation of the encoded ICP35 precursor.

It is contemplated that virtually any of the commonly employed eukaryotic host cells can be used in connection with herpes gene expression in accordance herewith. Examples include lines typically employed for eukaryotic expression such as AtT-20, HepG2, VERO, HeLa, CHO, WI 38, BHK, COS-7 RIN and MDCK cell lines. A preferred line for use in eukaryotic expression embodiments of the present invention is the BHK system.

Prokaryotic expression is an alternative which can be employed where desired. Although not required, where prokaryotic expression is envisioned, one will generally desire to employ a transcriptional unit which incorporates a reading frame corresponding only to the desired peptide itself, represented by embodiments in FIG. 1, so that further processing will not be required. Typically, prokaryotic promoters which may be employed include $P_LT7$ and lac promoter, with T7 being generally preferred. Other preferred bacterial expression vectors include plasmid PKK233-2 and PKK233-3, available from Pharmacia LKB Technology. These utilize the tac and trc promoters, respectively.

Of course, even where a eukaryotic hook-up and expression is used, one will nevertheless desire to include a prokaryotic origin of expression, as well as selective markers operable in prokaryotic systems, to allow "shuttling" of sequences from construction in prokaryotic to expression in eukaryotes.

In certain embodiments, one may desire to simply prepare herpes proteins or peptides in accordance with the present invention by non-recombinant synthetic means, such as by chemical synthesis of peptides or cell-free ribosomal "machine". Suitable peptide synthesizers are commercially available (Applied Biosystems), and may be employed.

In certain embodiments of the invention it is contemplated that DNA fragments both shorter and longer which incorporate sequences from FIG. 1 will find additional utilities, including uses in the preparation of short active peptides or even as short DNA fragment hybridization probes, e.g., in screening clone banks. In any event, fragments corresponding to the FIG. 1 sequence for stretches of as short as 14–20 or so nucleotides, will find utility in accordance with these or other embodiments. By having stretches of at least about 14 nucleotides in common with the nucleic acid segments of FIG. 1, or their complements, a DNA segment will have the ability to form a preferential hybrid with herpes species DNA, particularly under more stringent conditions such as 0.15M NaCl and 0.02M sodium citrate PH 7.4 at 50° C. While a complementary or common stretch of about 14 or so nucleotides will ensure the ability to form a stable hybrid, longer stretches of complementarity may prove more desirable for certain uses. Thus, one may desire for certain uses DNA segments incorporating longer stretches of complementarity, for example, on the order of 18, 22 or even 25 or so bases.

13. Antibodies Against the Proteins of the Present Invention

In other embodiments, the invention concerns the preparation of antibodies to the herpes protease and species derived therefrom, either recombinant or non-recombinantly prepared. For example, it is contemplated that antibodies prepared against the herpes protease of FIG. 1, or other non-human species such as bovine or porcine, will have certain advantages over antibodies prepared against the human species, particularly in embodiments where an immuno-binding of reduced strength is desired.

Compositions which include monoclonal antibodies of the present invention may be prepared by first fusing spleen cells of a rodent with myeloma cells from the same rodent species, wherein the rodent providing the spleen cells has been immunized with the herpes peptide, precursor, or related peptides. The rodent species utilized will generally be a mouse, particularly where one seeks to make an antibody against the herpes protease of FIG. 1. Of course, where a protease is prepared which incorporates structural variations over the one will likely be able to successfully employ a hybridoma system according to the species of interest. (See Materials and Methods.)

In addition, the present invention provides a method for isolating proteases from other species which may be found antigenically cross-reactive with that of HSV-1. This method includes preparing an immunoadsorbent material having attached thereto an antibody to the protease. Numerous immunoadsorbent materials are known to those skilled in the art and include, for example, Affi-Gel, Cn-Sepharose, protein A=Sepharose, and numerous other well known immunoadsorbent techniques. All such techniques are applicable to the present invention and should prove useful in the isolation of the immuno cross-reactive species (for a more complete listing, see *Monoclonal Hybridoma Antibodies: Techniques and Applications*, John G. Hurrell, ed., CRC Press, 1982, incorporated herein by reference).

Moreover, kits may be provided in accordance with the present invention to allow for a clinical detection of the herpes protease, and related proteases, in a biologic sample. Such kits would include polyclonal or monoclonal antibodies having specificity for the protease or immunologically related protease, in combination with an immunodetection reagent. An immunodetection reagent is defined as any reagent for detecting or quantifying the formation of antibody/antigen complexes. Typical immunodetection reagents include the use of radiolabeled or enzyme-labeled antigens or antibodies. Techniques which incorporate labeled antibodies include, for example, RIA (radioimmunoassay) and ELISA (enzyme-linked immuno assay). However, numerous other techniques are known which may be employed in immunodetection kits in accordance with the present invention Patents which teach suitable techniques include, for example, U.S. Pat. Nos. 4,446,232; 4,407,943; 4,399,299; and 454,233.

Thus, a typical herpes protease detection kit based on the ELISA technique could include the anti-herpes protease monoclonal antibody or purified protease antigen (where one seeks to detect circulating antibodies), and a second "immunodetection" antibody capable of specifically immunoreacting with the purified antigen or anti-protease antibody. The second antibody could have a color-generating enzymatic activity associated with it, for example, an attached peroxidase molecule. When a second "immunodetection" antibody is employed in this fashion, one will generally first form an immunocomplex between the biologic sample to be tested, for example, serum, plasma, urine or tissue samples, and the antibody. After forming such an immunocomplex, the immunodetection antibody is added to react quantitatively with protease-bound antibody. This complex formation is then quantitated through the colorimetric peroxidase assay.

An alternative to using the above double-antibody technique, one may incorporate the enzyme or radio-ligand directly on the anti-protease antibody, and quantification made directly with the use of this directly labeled antibody.

The foregoing type of kit and method is well known and can be viewed generally as including the steps of obtaining a biologic sample from a patient, contacting the biologic sample with anti-herpes protease monoclonal antibody under conditions which will promote the formation of antibody/antigen complexes and detecting the formation of a specific immunologic reaction between the monoclonal antibody and the sample.

Neutralizing antibodies are also contemplated which, when bound to the protease or a segment thereof, render the proteolytic capability of the protease non-functional.

14. Host Cell Cultures and Vectors

In general, prokaryotes are preferred for the initial cloning of DNA sequences and constructing the vectors useful in the invention. For example. *E. coli*. K12 strain 294 (ATCC No. 314460) is particularly useful. Other microbial strains which may be used include *E. coli*. strains such as *E. coli*. B, and *E. coli* X 1776 (ATTC No. 31537). These examples are, intended to be illustrative rather than limiting.

Prokaryotes may also be used for expression. The aforementioned strains, as well as *E. coli* W3110 (F-, lambda-, prototrophic, ATCC No. 273325), bacilli such as *Bacillus subtilus*, or other enterbacteriacea such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using PBR322, a plasmid derived from an *E. coli* a species pBR 322 contains genes for ampicillin and tetracycline resistance and thus provides easy means for identifying transformed cells. The PBR plasmid, or other microbial plasmid or phage must also contain, or be modified to contain, promoters which can be used by the microbial organism for expression of its own proteins.

The promoters most commonly used in recombinant DNA construction include the B-lactamase (penicillinase) and lactose promoter systems and a tryptophan (trp) promoter system. While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be used. *Saccharomyces cerevisiase*, or common baker's yeast is the most commonly used among eukaryotic microorganisms, although a number of other strains are commonly available. For expression in Saccharomyces. the plasmid Yrp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA termination. Other promoters, which have the additional advantage of transcription controlled by growth conditions are the promoter region for alcohol dehydrogenase 2, isocytochrome C, acid phosphatase, degradative enzyres associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20 VERO and Hela cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bg1 site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, HSV, BPV, CMV source, or may be provided by the host cell chromosomal replication mechanism. If the vector is integrated into the host cell chromosome, the latter is often sufficient.

15. Nucleic Acid Hybridization to Detect the Sequences Capable of Coding for the Serine Proteases, the ICP35 Proteins or their Biologically Functional Equivalents The nucleic acid sequence information provided by the invention allows for the preparation of relatively short DNA (or RNA) sequences having the ability to specifically hybridize to gene sequences capable of coding for at least the proteolytic domain of the proteases or the cleavage site of the ICP35 problems. In these aspects, nucleic acid probes of an appropriate length are prepared based on a consideration of the sequence shown in FIG. 1B (SEQ ID NO: 1). The ability of such nucleic acid probes to specifically hybridize to the proteases or ICP35 gene sequences lend them particular utility in a variety of embodiments. Most importantly, the probes can be used in a variety of assays for detecting the presence of complementary sequences in a given sample. Other uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 14 base nucleotide stretches of the sequence shown in FIG. 1B (SEQ ID NO: 1). A size of at least 14 nucleotides in length helps to ensure that the fragment will be of sufficient length to form a duplex molecule that is both stable and selective. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production. Segments of from 18 to 25, or even 30 to 40 bases are also within the scope of this invention.

Accordingly, the nucleotide sequences of the invention are important for their ability to selectively form duplex molecules with complementary stretches of the gene. Depending on the application envisioned, varying conditions of hybridization may be employed to achieve varying degree of selectivity of the probe toward the target sequence. For applications requiring a high degree of selectivity, relatively stringent conditions may be employed to form the hybrids, for example, selecting relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, preparation of mutants employing a mutant primer strand hybridized to an underlying template, or to isolate protease or ICP35 coding sequences from related species, functional equivalents, or the like, less stringent hybridization conditions are called for in order to allow formation of the heteroduplex. In these circumstances, conditions employed would be, e.g., such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, an enzyme tag such as urease, alkaline phosphatase or peroxidase, may be employed instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

One method of making molecules for detection of cell extracts is to use fluorescent probes. Fluorescent probes are well known to those skilled in the art. An example of a method is to bind fluorescein-labeled avidin (Vector Laboratories, Burlingame, Calif.) to a biotin-labeled protein. The signal may be enhanced.

REFERENCES

The references listed below are incorporated herein by reference to the extent that they supplement, explain, provide a background for, or teach methodology, techniques, and/or compositions employed herein.

| | |
|---|---|
| Reference 1. | Arsenakis, M., Hubenthal-Voss, J., Campadelli-Fiume, G., Pereira, L., and Roizman, B. (1986). Construction and properties of a cell line constitutively expressing the herpes simplex virus glycoprotein B dependent on functional α4 protein synthesis. J. Virol. 60:674–682. |
| Reference 2. | Batterson, W. and Roizman, B. Characterization of the herpes simplex virion-associated factor responsible for the induction of α genes. J. Virol. 46:371–377, 1983. |
| Reference 3. | Braun, D. K., Pereira L., Norrild, B., and Roizman, B. (1983). Application of denatured, electrophoretically separated, and immobilized lysates of herpes simplex virus-infected cells for the detection of monoclonal antibodies and for studies of the properties of viral proteins. J. Virol. 46:103–112. |
| Reference 4. | Braun, D. K., Roizman, B., and Pereira, L. (1984). Characterization of post-transnational products of herpes simplex virus gene 35 proteins binding to the surfaces of full capsids but not empty capsids. J. Virol. 49:142–153. |
| Reference 5. | Corey, L and Spear, (1986). PG Infections with herpes simplex viruses. N. Eng. J. Med. 314:686–691. |
| Reference 6. | Davison, A. J. and McGeoch, D. J. (1986). Evolutionary comparisons of the S segments in the genomes of herpes simplex virus type 1 and *varicella-zoster* virus. J. Gen. Virol. 67:597–611. |
| Reference 7. | Ejercito, P. M., Kieff, E. D., and Roizman, B. (1986). Characterization of herpes simplex virus strains differing in their effect on social behavior of infected cells. J. Gen. Virol. 2:357–364. |
| Reference 8. | Gibson, W., Marcy, A. I., Comolli, J. C., and Lee, J. (1990). Identification of precursor to cytomegalovirus capsid assembly protein and evidence that processing results in loss of its carboxyl-terminal end. J. Virol. 64:1241:1249. |
| Reference 9. | Gibson, W., and Roizman, B. (1972). Proteins specified by herpes simplex virus VIII. Characterization and composition of multiple capsid forms of subtypes 1 and 2. J. Virol. 10:1044–1052. |
| Reference 10. | Gibson, W., and Roizman, B. (1974). Protein specified by herpes simplex virus. Staining and radiolabeling properties of B capsids and virion proteins in polyacrylamide gels. J. Virol. 13:155–165. |
| Reference 11. | Jenkins et al. (1984). Characterization of the mRNAs mapping in the Bp1II N fragment of the herpes simplex virus type 2 genome. J. Virol. 52:99–107. |
| Reference 12. | Kristie, T. M., and Roizman, B. (1984). Separation of sequences defining basal expressing from those conferring α gene recognition within the regulatory domains of herpes simplex virus 1 α genes. Proc. Natl. Acad. Sci. USA, 81:4065–4069. |
| Reference 13. | Liu, F., and Roizman, B. (1991). The promoter, transcriptional unit, and coding sequence of herpes simplex family 35 proteins are contained within and in frame with the $U_L26$ open reading frame. J. Virol. 65:206–212. |
| Reference 14. | McGeoch, D. J., Dalrymple, M. A., Davison, A. J., Dolan, A., Frame, M. C., McNab, D., Perry, L. J., Scott, J. E., and Taylor, P. (1988). The complete DNA sequence of the long unique region in the genome of herpes simplex virus type 1. J. Gen. Virol. 69:1531–1574. |
| Reference 15. | Morse, L. S., Pereira, L., Roizman, B. et al. (1978). Preparation of herpes simplex virus of high titer. J. Virol. 2:83–84. |
| Reference 16. | Newcomb, W. W., and Brown, J. C. (1991). Structure of the herpes simplex virus capsid effects of extraction with guanidine hydrochloride and partial reconstitution of extracted capsids. J. Virol. 65:613–620. |
| Reference 17. | Newcomb, W. W., Brown, J. C., Booy, F. P., and Steven, A. C. (1989). Nucleocapsid mass and capsomere protein stoichiometry in equine herpes virus 1: scanning transmission electron microscopic study. J. Virol. 63:3777–3783. |
| Reference 18. | Post, L. E., Mackem, S. and Roizman, B. (1981). The regulation of α genes of herpes simplex virus: expression of chimeric genes produced by fusion of thymidine kinase with α gene promoters. Cell 24:555–565. |
| Reference 19. | Preston, V. G., J. A. V. Coates, and Rixon, F. J. (1983). Identification and characterization of a herpes simplex virus gene product required for encapsodation of virus DNA. J. Virol. 45:1056–1064. |
| Reference 20. | Robson, L. and Gibson, W. (1989). Primate cytomegalovirus assembly protein: genome localization and nucleotide sequence. J. Virol. 63:669–676. |
| Reference 21. | Roizman, B., and Spear, P. ZG. (1968). Preparation of herpes simplex virus of high titer. J. Virol. 65:1525–1529. |

What is claimed is:

1. An isolated and purified nucleic acid molecule comprising a fragment consisting of a sequence encoding a herpes simplex 1 protease, said molecule being engineered through the introduction of one or more genetic control elements to control the expression of said coding sequence, wherein said control element is one that does not normally control expression of the herpes virus protease in the herpes virus genome.

2. The nucleic acid molecule of claim 1 that comprises an overlapping first and a second open reading frame, said molecule coding for a first and a second protein respectively, wherein the first protein has an apparent molecular weight of approximately 75–85 kd and the second protein has an apparent molecular weight of approximately 40 kd–55 kd, both molecular weights as determined by SDS-polyacrylamide gel electrophoresis, and wherein the first protein comprises at least a proteolytic module capable of cleaving the first or the second protein.

3. The nucleic acid molecule of claim 2 wherein the length of the coding region for the second protein is approximately 990 base pairs.

4. The nucleic acid molecule of claim 2 comprising a promoter sequence for the second protein.

5. A promoter of approximately 135–168 base pairs in length located within the HpaI-PstI cleavage sites in the first open reading frame of claim 2, and capable of initiating expression of the second protein of claim 2.

6. The nucleic acid molecule of claim 1 that is a DNA molecule.

7. The nucleic acid molecule of claim 1 comprising a map region essentially as set forth in FIG. 1, line 5 or line 6.

8. The nucleic acid molecule of claim 1 that encodes an mRNA which initiates at approximately nucleotide position +1000 as distanced from the herpes $U_L26$ transcription initiation site designated (+1), said RNA being translated from the methionine initiation codon located at position +1099 of the $U_L26$ transcriptional unit.

9. The nucleic acid molecule of claim 1 wherein the nucleotide is RNA.

10. The nucleic acid molecule of claim 1 comprising less than about 4600 nucleotides.

11. The nucleic acid molecule of claim 1 comprising less than about 3500 nucleotides.

12. The nucleic acid molecule of claim 1 wherein the fragment comprises less than about 2600 nucleotides.

13. The nucleic acid molecule of claim 1 wherein the fragment comprises less than about 1900 nucleotides.

14. The nucleic acid molecule of claim 1 wherein the fragment comprises the nucleotide sequence shown in SEQ ID NO. 1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1905 base pairs
      (B) TYPE: nucleic acid
      (C) STRANDEDNESS: double (D) TOPOLOGY: linear (xi) SEQUENCE DESCRIPTION: SEQ ID NO:1:

```
ATGGCAGCCG ATGCCCCGGG AGACCGGATG GAGGAGCCCC TGCCCGACAG GGCCGTGCCC      60
ATTTACGTGG CTGGGTTTTT GGCCCTGTAT GACAGCGGGG ACTCGGGCGA GTTGGCATTG     120
GATCCGGATA CGGTGCGGGC GGCCCTGCCT CCGGATAACC CACTCCCGAT TAACGTGGAC     180
CACCGCGCTG GCTGCGAGGT GGGGCGGGTG CTGGCCGTGG TCGACGACCC CCGCGGGCCG     240
TTTTTTGTGG GGCTGATCGC CTGCGTGCAG CTGGAGCGCG TCCTCGAGAC GGCCGCCAGC     300
GCTGCGATTT TCGAGCGCCG CGGGCCGCCG CTCTCCCGGG AGGAGCGCCT GTTGTACCTG     360
ATCACCAACT ACCTGCCCTC GGTCTCCCTG GCCACAAAAC GCCTGGGGGG CGAGGCGCAC     420
CCCGATCGCA CGCTGTTCGC GCACGTCGCG CTGTGCGCGA TCGGGCGGCG CCTCGGCACT     480
ATCGTCACCT ACGACACCGG TCTCGACGCC GCCATCGCGC CCTTTCGCCA CCTGTCGCCG     540
GCGTCTCGCG AGGGGCGCG GCGACTGGCC GCCGAGGCCG AGCTCGCGCT GTCCGGGCGC     600
ACCTGGGCGC CCGGCGTGGA GGCGCTGACC CACACGCTGC TTTCCACCGC CGTTAACAAC     660
ATGATGCTGC GGGACCGCTG GAGCCTGGTG GCCGAGCGGC GGCGGCAGGC CGGGATCGCC     720
GGACACACCT ACCTCCAGGC GAGCGAAAAA TTCAAAATGT GGGGGGCGGA GCCTGTTTCC     780
GCGCCGGCGC GCGGGTATAA GAACGGGGCC CCGGAGTCCA CGGACATACC GCCCGGCTCG     840
ATCGCTGCCG CGCCGCAGGG TGACCGGTGC CCAATCGTCC GTCAGCGCGG GGTCGCCTTG     900
TCCCCGGTAC TGCCCCCCAT GAACCCCGTT CCGACATCGG GCACCCCGGC CCCCGCGCCG     960
CCCGGCGACG GGAGCTACCT GTGGATCCCG GCCTCCCATT ACAACCAGCT CGTCGCCGGC    1020
CATGCCGCGC CCCAACCCCA GCCGCATTCC GCGTTTGGTT TCCCGGCTGC GGCGGGGTCC    1080
GTGGCCTATG GCCTCACGG TGCGGGTCTT TCCCAGCATT ACCCTCCCCA CGTCGCCCAT    1140
CAGTATCCCG GGGTGCTGTT CTCGGGACCC AGCCCACTCG AGGCGCAGAT AGCCGCGTTG    1200
GTGGGGGCCA TAGCCGCGGA CCGCCAGGCG GGCGGTCAGC CGGCCGCGGG AGACCCTGGG    1260
GTCCGGGGGT CGGGAAAGCG TCGCCGGTAC GAGGCGGGGC CGTCGGAGTC CTACTGCGAC    1320
CAGGACGAAC CGGACGCGGA CTACCCGTAC TACCCCGGGG AGGCTCGAGG CGCGCCGCGC    1380
GGGGTCGACT CCCGGCGCGC GGCCCGCCAT TCTCCCGGGA CCAACGAGAC CATCACGGCG    1440
CTGATGGGGG CGGTGACGTC TCTGCAGCAG GAACTGGCGC ACATGCGGGC TCGGACCAGC    1500
GCCCCTATG GAATGTACAC GCCGGTGGCG CACTATCGCC CTCAGGTGGG GGAGCCGGAA    1560
CCAACAACGA CCCACCCGGC CCTTTGTCCC CCGGAGGCCG TGTATCGCCC CCCACCACAC    1620
AGCGCCCCCT ACGGTCCTCC CCAGGGTCCG GCGTCCCATG CCCCCACTCC CCCGTATGCC    1680
CCAGCTGCCT GCCCGCCAGG CCCGCCACCG CCCCCATGTC CTTCCACCCA GACGCGCGCC    1740
CCTCTACCGA CGGAGCCCGC GTTCCCCCCC GCCGCCACCG GATCCCAACC GGAGGCATCC    1800
AACGCGGAGG CCGGGGCCCT TGTCAACGCC AGCAGCGCAG CACACGTGGA CGTTGACACG    1860
GCCCGCGCCG CCGATTTGTT CGTCTCTCAG ATGATGGGGG CCCGC                   1905
```

(2) INFORMATION FOR SEQ ID NO:2:

(i) SEQUENCE CHARACTERISTICS:
        (A) LENGTH: 635 amino acids
        (B) TYPE: amino acid
        (C) STRANDEDNESS: single
        (D) TOPOLOGY: linear (xi) SEQUENCE DESCRIPTION: SEQ ID NO:2:

-continued

```
Met Ala Ala Asp Ala Pro Gly Asp Arg Met Glu Glu Pro Leu Pro Asp
1               5                   10                  15

Arg Ala Val Pro Ile Tyr Val Ala Gly Phe Leu Ala Leu Tyr Asp Ser
            20                  25                  30

Gly Asp Ser Gly Glu Leu Ala Leu Asp Pro Asp Thr Val Arg Ala Ala
        35                  40                  45

Leu Pro Pro Asp Asn Pro Leu Pro Ile Asn Val Asp His Arg Ala Gly
    50                  55                  60

Cys Glu Val Gly Arg Val Leu Ala Val Val Asp Asp Pro Arg Gly Pro
65                  70                  75                  80

Phe Phe Val Gly Leu Ile Ala Cys Val Gln Leu Glu Arg Val Leu Glu
                85                  90                  95

Thr Ala Ala Ser Ala Ala Ile Phe Glu Arg Arg Gly Pro Pro Leu Ser
            100                 105                 110

Arg Glu Glu Arg Leu Leu Tyr Leu Ile Thr Asn Tyr Leu Pro Ser Val
        115                 120                 125

Ser Leu Ala Thr Lys Arg Leu Gly Gly Glu Ala His Pro Asp Arg Thr
    130                 135                 140

Leu Phe Ala His Val Ala Leu Cys Ala Ile Gly Arg Arg Leu Gly Thr
145                 150                 155                 160

Ile Val Thr Tyr Asp Thr Gly Leu Asp Ala Ala Ile Ala Pro Phe Arg
                165                 170                 175

His Leu Ser Pro Ala Ser Arg Glu Gly Ala Arg Arg Leu Ala Ala Glu
            180                 185                 190

Ala Glu Leu Ala Leu Ser Gly Arg Thr Trp Ala Pro Gly Val Glu Ala
        195                 200                 205

Leu Thr His Thr Leu Leu Ser Thr Ala Val Asn Asn Met Met Leu Arg
    210                 215                 220

Asp Arg Trp Ser Leu Val Ala Glu Arg Arg Gln Ala Gly Ile Ala
225                 230                 235                 240

Gly His Thr Tyr Leu Gln Ala Ser Glu Lys Phe Lys Met Trp Gly Ala
                245                 250                 255

Glu Pro Val Ser Ala Pro Ala Arg Gly Tyr Lys Asn Gly Ala Pro Glu
            260                 265                 270

Ser Thr Asp Ile Pro Pro Gly Ser Ile Ala Ala Pro Gln Gly Asp
    275                 280                 285

Arg Cys Pro Ile Val Arg Gln Arg Gly Val Ala Leu Ser Pro Val Leu
290                 295                 300

Pro Pro Met Asn Pro Val Pro Thr Ser Gly Thr Pro Ala Pro Ala Pro
305                 310                 315                 320

Pro Gly Asp Gly Ser Tyr Leu Trp Ile Pro Ala Ser His Tyr Asn Gln
                325                 330                 335

Leu Val Ala Gly His Ala Ala Pro Gln Pro Gln Pro His Ser Ala Phe
            340                 345                 350

Gly Phe Pro Ala Ala Gly Ser Val Ala Tyr Gly Pro His Gly Ala
        355                 360                 365

Gly Leu Ser Gln His Tyr Pro Pro His Val Ala His Gln Tyr Pro Gly
    370                 375                 380

Val Leu Phe Ser Gly Pro Ser Pro Leu Glu Ala Gln Ile Ala Ala Leu
385                 390                 395                 400

Val Gly Ala Ile Ala Ala Asp Arg Gln Ala Gly Gln Pro Ala Ala
                405                 410                 415

Gly Asp Pro Gly Val Arg Gly Ser Gly Lys Arg Arg Arg Tyr Glu Ala
```

-continued

```
            420                 425                 430

Gly Pro Ser Glu Ser Tyr Cys Asp Gln Asp Glu Pro Asp Ala Asp Tyr
        435                 440                 445

Pro Tyr Tyr Pro Gly Glu Ala Arg Gly Ala Pro Arg Gly Val Asp Ser
    450                 455                 460

Arg Arg Ala Ala Arg His Ser Pro Gly Thr Asn Glu Thr Ile Thr Ala
465                 470                 475                 480

Leu Met Gly Ala Val Thr Ser Leu Gln Gln Glu Leu Ala His Met Arg
                485                 490                 495

Ala Arg Thr Ser Ala Pro Tyr Gly Met Tyr Thr Pro Val Ala His Tyr
            500                 505                 510

Arg Pro Gln Val Gly Glu Pro Glu Pro Thr Thr Thr His Pro Ala Leu
        515                 520                 525

Cys Pro Pro Glu Ala Val Tyr Arg Pro Pro Pro His Ser Ala Pro Tyr
    530                 535                 540

Gly Pro Pro Gln Gly Pro Ala Ser His Ala Pro Thr Pro Pro Tyr Ala
545                 550                 555                 560

Pro Ala Ala Cys Pro Pro Gly Pro Pro Pro Pro Pro Cys Pro Ser Thr
                565                 570                 575

Gln Thr Arg Ala Pro Leu Pro Thr Glu Pro Ala Phe Pro Pro Ala Ala
            580                 585                 590

Thr Gly Ser Gln Pro Glu Ala Ser Asn Ala Glu Ala Gly Ala Leu Val
        595                 600                 605

Asn Ala Ser Ser Ala Ala His Val Asp Val Asp Thr Ala Arg Ala Ala
    610                 615                 620

Asp Leu Phe Val Ser Gln Met Met Gly Ala Arg
625                 630                 635
```